United States Patent
Farace et al.

(10) Patent No.: US 12,031,174 B2
(45) Date of Patent: Jul. 9, 2024

(54) METHODS FOR MEASURING BACTERIA IN BIOLOGICAL SAMPLES

(71) Applicant: IDEXX LABORATORIES, INC., Westbrook, ME (US)

(72) Inventors: Giosi Farace, Georgetown, ME (US); Jon Braff, Portland, ME (US); Murthy V S N Yerramilli, Falmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 1006 days.

(21) Appl. No.: 16/362,478

(22) Filed: Mar. 22, 2019

(65) Prior Publication Data

US 2019/0316171 A1 Oct. 17, 2019

Related U.S. Application Data

(60) Provisional application No. 62/646,588, filed on Mar. 22, 2018.

(51) Int. Cl.
| | | |
|---|---|---|
| *C12Q 1/06* | (2006.01) | |
| *C12Q 1/22* | (2006.01) | |
| *C12Q 1/24* | (2006.01) | |
| *G01N 15/02* | (2006.01) | |
| *G01N 15/0227* | (2024.01) | |
| *G01N 33/493* | (2006.01) | |
| *G01N 33/52* | (2006.01) | |

(52) U.S. Cl.
CPC ............... *C12Q 1/06* (2013.01); *C12Q 1/22* (2013.01); *C12Q 1/24* (2013.01); *G01N 15/0227* (2013.01); *G01N 33/493* (2013.01); *G01N 33/52* (2013.01); *G01N 2015/0294* (2013.01); *G01N 2800/26* (2013.01)

(58) Field of Classification Search
CPC ............. C12Q 1/06; C12Q 1/24; C12Q 1/22; G01N 33/52; G01N 33/493; G01N 15/0227; G01N 2800/26; G01N 2015/0294
See application file for complete search history.

(56) References Cited

U.S. PATENT DOCUMENTS

| | | |
|---|---|---|
| 3,971,703 A | 7/1976 | Picciolo et al. |
| 4,610,961 A | 9/1986 | Guardino et al. |
| 5,364,763 A | 11/1994 | Kacian |
| 5,891,733 A | 4/1999 | Inoue |
| 5,902,731 A | 5/1999 | Ouyang et al. |
| 6,897,037 B2 | 5/2005 | Okada et al. |
| 7,298,886 B2* | 11/2007 | Plumb .................... G06V 20/69 382/133 |
| 9,915,813 B2 | 3/2018 | Olesen et al. |
| 9,982,041 B2 | 5/2018 | Wong et al. |
| 10,128,078 B2 | 11/2018 | Hariyama et al. |
| 10,131,902 B2 | 11/2018 | Kreader |
| 2002/0076743 A1 | 6/2002 | Sakai et al. |
| 2003/0022270 A1 | 1/2003 | Seaver et al. |
| 2009/0081638 A1* | 3/2009 | Bergwerff ........ G01N 33/56911 435/7.1 |
| 2012/0165626 A1* | 6/2012 | Irina ................... A61B 5/14532 600/362 |
| 2016/0024559 A1* | 1/2016 | Sangha .................. G01N 1/405 422/547 |
| 2016/0363588 A1 | 12/2016 | Kawano |

FOREIGN PATENT DOCUMENTS

| | | |
|---|---|---|
| EP | 0285439 B1 | 10/1988 |
| JP | S59-120100 A | 7/1984 |
| JP | 2000-116396 A | 4/2000 |
| JP | 2001-258590 A | 9/2001 |
| JP | 2013-513087 A | 4/2013 |
| JP | 2017201289 A | 11/2017 |
| JP | 2002-357599 A | 12/2022 |
| WO | 2004/059280 A2 | 7/2004 |
| WO | 2007/044978 A1 | 4/2007 |
| WO | 2012/168003 A1 | 12/2012 |
| WO | 2015/115502 A1 | 8/2015 |
| WO | 2015/129870 A1 | 9/2015 |
| WO | 2015/179976 A1 | 12/2015 |

OTHER PUBLICATIONS

APHL article on AFB smear microscopy (2013, 67 pages. (Year: 2013).*
Tan et al. Thermodynamics of Sodium Dodecyl Sulfate Partitioning into Lipid Membranes. Biophysical Journal (2002), 83(3), 1547-1556. (Year: 2002).*
The International Search Report for PCT/US2019/023732, 5 pages, dated Jul. 23, 2019.
Aja, et al., "Are we doing out part to prevent superbugs?" Vet. Emerg. Top. Rep. 1-23 (2017).
Anonymous, "Kidney patients' urine may predict death risk" Indo-Asian News Service (2017).
Harley et al., "Proteinuria in dogs and cats" Can. Vet. J. 53: 631-638 (2012).
Parikh et al., "Urine microscopy is associated with severity and worsening of acute kidney injury in hospitalized patients" Clin. J. Am. Nephrol 5(3): 402-408 (2010).

* cited by examiner

*Primary Examiner* — Sean C. Barron
(74) *Attorney, Agent, or Firm* — McDonnell Boehnen Hulbert & Berghoff LLP

(57) ABSTRACT

The disclosure relates generally to methods for measuring bacteria in biological samples. More particularly, the disclosure relates to methods for measuring bacteria using an aqueous clearance solution.

37 Claims, 13 Drawing Sheets

A

B

Untreated

SMOT

Methyl Stearoyl Taurate

Untreated

Treated

Treated with 4 min incubation

Untreated

Treated

Untreated

Treated

METHODS FOR MEASURING BACTERIA IN BIOLOGICAL SAMPLES

CROSS-REFERENCE TO RELATED APPLICATIONS

This application claims the benefit of priority of U.S. Provisional Patent Application No. 62/646,588, filed Mar. 22, 2018, which is incorporated by reference in its entirety.

BACKGROUND

1. Field of the Disclosure

The disclosure relates to methods for measuring bacteria in biological samples.

2. Technical Background

Quantification of bacteria, yeast, and other organisms in fluid can be useful for medical diagnosis, drug development, industrial hygiene, food safety, and many other fields. For example, the amount of bacteria in urine is an important parameter in clinical diagnosis of an infection. In general, the presence of bacteria of $10^5$/mL or more in urine is recognized as a criterion of positive urinary tract infection. Urine samples having $10^3$/mL or fewer bacteria are considered negative for urinary tract infection (i.e., as having normal bacteria flora). If the urine sample has about $10^4$/mL bacteria, however, no diagnosis is established and the sample is often re-tested.

Urine often contains contaminants such as sediment, debris, mucus threads, crystals, amorphous salts, patient cells, red blood cells, and cell fragments. Some of the many contaminants are provided in FIG. 1. These substances hinder the measurement of other types of particles (in particular bacteria) so that it has been difficult to accurately count the number of bacteria. Conventionally, observation of bacteria in urine has been performed by microscopic examination of stained bacteria. Bacterial staining also results in contaminants being stained simultaneously, and hinders the accurate measurement of the amount of bacteria.

Accordingly, there is a need for improved systems and methods that quickly determine whether bacteria are present in the fluid sample and determine the amount of bacteria. There is also a need for an improved systems and methods that more quickly determine the type of bacteria after it is determined that bacteria are present.

SUMMARY

One aspect of the disclosure provides methods of measuring bacteria in a biological sample. These methods include
  contacting the biological sample with an aqueous clearance solution comprising one or more surfactants; and
  determining bacteria in the sample.

In certain embodiments of this aspect, the surfactant is sodium methyl oleoyl taurate or a derivative thereof.

Another aspect of the disclosure provides methods for clearing non-bacterial particulate matter from a biological sample. These methods include contacting the biological sample with an aqueous clearance solution comprising one or more surfactants.

In certain embodiments of this aspect, the surfactant is sodium methyl oleoyl taurate or a derivative thereof.

Another aspect of the disclosure provides methods of measuring bacteria in a biological sample. These methods include
  analyzing a first portion of the biological sample for bacteria in the first portion;
  determining that the presence or amount of non-bacterial particulate matter interferes with the analysis for bacteria;
  contacting a second portion of the biological sample with an aqueous clearance solution comprising one or more surfactants; and
  determining bacteria in the second portion of the biological sample.

In one aspect, methods of the disclosure as described herein reduce ambiguous results in measuring bacteria in a biological sample.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE DRAWINGS

The accompanying drawings are included to provide a further understanding of the methods and devices of the disclosure, and are incorporated in and constitute a part of this specification. The drawings are not necessarily to scale, and sizes of various elements may be distorted for clarity. The drawings illustrate one or more embodiment(s) of the disclosure, and together with the description, serve to explain the principles and operation of the disclosure.

DETAILED DESCRIPTION

Figure 1:
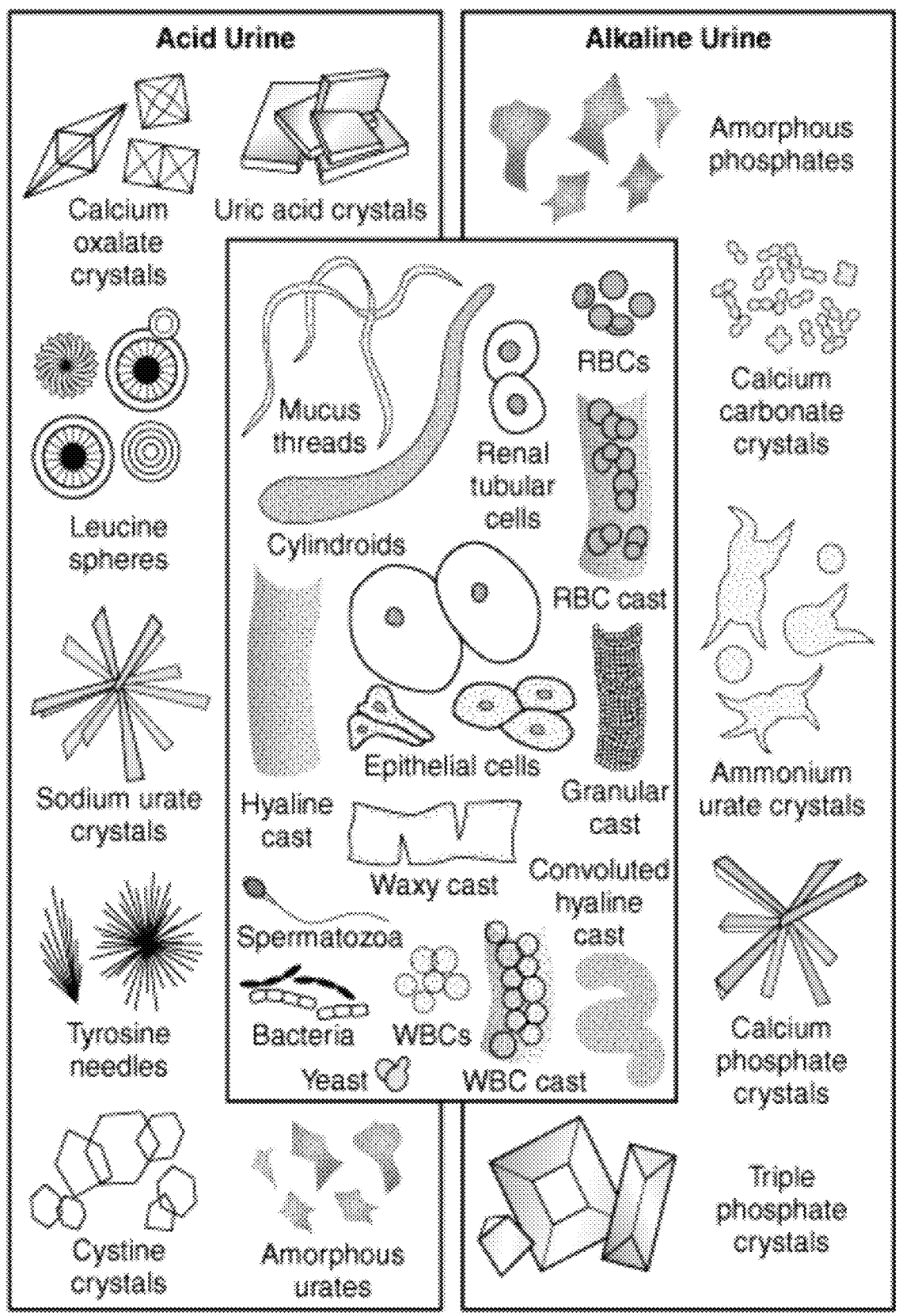
FIG. 1 illustrates most common urine contaminants.

The disclosure provides materials, methods, and apparatus to improve the measurement of an amount of bacteria in biological and other samples. For instance, the disclosure describes efficient, accurate, and cost-effective methods for minimizing the effect of the contaminants that can affect the accuracy of the measurement. For example, urine often contains contaminants, such as those shown in FIG. 1, that interfere with the accurate measurement of the amount of bacteria. Accordingly, the method of the disclosure eliminates the interference caused by common urine contaminants (e.g., sediment, debris, mucus threads, crystals, amorphous salts, cell fragments, red blood cells, and patient cells) and allows for accurate measurement of bacteria. In a particular example of the methods of the disclosure include treating the sample to render the contaminants optically clear in the treated sample so that the accurate measurement of bacteria only can be accomplished. In addition, some embodiments of the methods of the disclosure are able to distinguish between two shapes of bacteria, rod and coccus, as well as cocci such as diplococci and cocci chains. Furthermore, in the methods of the disclosure, the bacteria in a biological sample may be measured using a single sample, a single image, and/or a single assay. As a result, the methods of the disclosure may eliminate multiple test methods, extensive sample handling, shipping, and storage. The measurements can be performed in-clinic and in real-time resulting in fewer changes to the sample.

As used herein, "measuring" or "measurement" of bacteria is not intended to be limiting and may involve determining the amount of bacteria (e.g., a total number of cells or a concentration), counting the bacteria, determining the size and/or shape of the bacteria, and/or determining the ability of the bacteria to be stained or labeled.

Thus, one aspect of the disclosure provides a method of measuring an amount of bacteria in a biological sample. The method includes contacting the biological sample with an aqueous clearance solution comprising one or more surfactants; and determining the amount of bacteria in the sample. Such method, in certain embodiments, reduces ambiguous results in measuring bacteria in a biological sample.

Another aspect of the disclosure provides a method for clearing non-bacterial particulate matter from a biological sample. The non-bacterial particulate matter includes, but is not limited to, sediment, debris, mucus threads, crystals, amorphous salts, cell fragments, red blood cells, and patient cells. This method includes contacting the biological sample with an aqueous clearance solution comprising one or more surfactants. Such method, in certain embodiments, reduces ambiguous results in measuring bacteria in a biological sample.

As described above, the methods as described herein are carried out on a biological sample. In some embodiments of the methods of the disclosure, the sample is a urine sample. In some embodiments of the methods of the disclosure, the sample is a blood sample (whole blood, serum, or plasma).

In the methods of the disclosure, the biological sample is contacted with an aqueous clearance solution. Water is primarily used in the aqueous solutions of the disclosure (e.g., in the aqueous clearance solution or the aqueous chelator solution). However, in addition to water, aqueous solutions may include one or more organic solvents. In certain embodiments, the aqueous solution is a water solution. In certain embodiments, the aqueous solution comprises water and one or more organic solvents (such as alcohols, dimethyl sulfoxide, dimethylformamide, and acetone). The one or more organic solvents may be present at a concentration of 0-70% volume/volume in the aqueous solution. One of skill in the art will be able to select suitable concentrations, based in part on the limits of solubility.

The aqueous clearance solution of the disclosure comprises one or more surfactants. While the surfactant is generally described herein in the singular, a plurality of surfactants can be formulated together to provide the aqueous clearance solution of the disclosure. When two or more surfactants are used in the aqueous clearance solution, the relative amounts of the two can be varied based on the disclosure herein, depending on the performance desired. In certain embodiments, the weight ratio of a first surfactant to a second surfactant is in the range of 1:9 to 9:1.

Based on the disclosure herein, the surfactant can be selected to provide the aqueous clearance solution with desirable performance in eliminating interference caused by common urine contaminants. Moreover, the surfactant can be selected to avoid (e.g., prevent or not cause) the formation of micelles that are visible by light microscopy under the conditions of the methods of the disclosure. Such micelles can cause interference and appear substantially similar to bacteria when observed by light microscopy. Thus, in certain embodiments, the surfactant can be selected to avoid the formation of micelles that are substantially similar to bacteria by light microscopy.

Various surfactants are known in the art and can suitably be used in the methods and compositions described herein. In certain embodiments a, the surfactant is a N-methyltaurine derivative (e.g., a fatty acid amide) or a salt thereof. Suitable derivatives of N-methyltaurine include compounds having one or more chemical structure features of, for example, methyl oleoyl taurate provided below, such as an unsaturated hydrocarbon chain and/or taurate head group (which may be further substituted). Examples of unsaturated hydrocarbon chains include, but are not limited to those derived from oleic acid, linoleic acid, α-linolenic acid, stearidonic acid, eicosapentaenoic acid, docosahexaenoic acid, γ-linolenic acid, dihomo-γ-linolenic acid, arachidonic acid, docosatetraenoic acid, palmitoleic acid, paullinic acid, gondoic acid, erucic acid, nervonic acid, mead acid, linolelaidic acid, vaccenic acid, elaidic acid, myristoleic acid, sapienic acid, petroselinic acid, docosenoic acid, or gadolenic acid.

For example, the N-methyltaurine derivative may be represented by the following general formula:

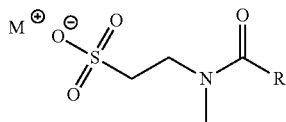

wherein $M^+$ is a cation and R is a monounsaturated or polyunsaturated $C_{10}$-$C_{22}$ hydrocarbyl.

For purposes of this disclosure, "hydrocarbyl" is defined to be a monovalent group containing carbon and hydrogen, which may be linear or branched. Monounsaturated hydrocarbyl is defined as a hydrocarbyl having one double bond or one triple bond. In preferred embodiment, monounsaturated hydrocarbyl is a hydrocarbyl having one double bond. Polyunsaturated hydrocarbyl is defined as a hydrocarbyl having two or more double bonds, triple bonds, or combinations thereof. Any double bond in the hydrocarbyl group may be in the cis or trans configuration. In a preferred embodiment, at least one of the one or more double bonds is in the cis configuration.

In certain embodiment, R is monounsaturated (e.g., having one double bond) $C_{10}$-$C_{22}$ hydrocarbyl (e.g., $C_{10}$-$C_{20}$ hydrocarbyl, $C_{10}$-$C_{18}$ hydrocarbyl, $C_{10}$-$C_{16}$ hydrocarbyl, $C_{10}$-$C_{14}$ hydrocarbyl, $C_{10}$-$C_{12}$ hydrocarbyl, $C_{14}$-$C_{22}$ hydrocarbyl, $C_{14}$-$C_{20}$ hydrocarbyl, $C_{14}$-$C_{18}$ hydrocarbyl, $C_{14}$-$C_{16}$ hydrocarbyl, $C_{18}$-$C_{22}$ hydrocarbyl, $C_{18}$-$C_{20}$ hydrocarbyl, $C_{16}$-$C_{18}$ hydrocarbyl, $C_{18}$-$C_{22}$ hydrocarbyl, or $C_{18}$-$C_{22}$ hydrocarbyl). In certain embodiments, R is cis-monounsaturated $C_{10}$-$C_{22}$ hydrocarbyl (e.g., $C_{10}$-$C_{20}$ hydrocarbyl, $C_{10}$-$C_{18}$ hydrocarbyl, $C_{10}$-$C_{16}$ hydrocarbyl, $C_{10}$-$C_{14}$ hydrocarbyl, $C_{10}$-$C_{12}$ hydrocarbyl, $C_{14}$-$C_{22}$ hydrocarbyl, $C_{14}$-$C_{20}$ hydrocarbyl, $C_{14}$-$C_{18}$ hydrocarbyl, $C_{14}$-$C_{16}$ hydrocarbyl, $C_{16}$-$C_{22}$ hydrocarbyl, $C_{16}$-$C_{20}$ hydrocarbyl, $C_{16}$-$C_{18}$ hydrocarbyl, $C_{18}$-$C_{22}$ hydrocarbyl, or $C_{18}$-$C_{22}$ hydrocarbyl).

$M^+$ may be any suitable cation as provided herein. Examples include, but are not limited to, $Na^+$, $K^+$, $Mg^{2+}$, $Ca^{2+}$, and $NH_4^+$. In certain embodiments, $M^+$ is $Na^+$.

In certain embodiments as otherwise described herein, the surfactant is a salt of methyl oleoyl taurate. Sodium salt of methyl oleoyl taurate (sodium methyl oleoyl taurate or SMOT) has the following structure:

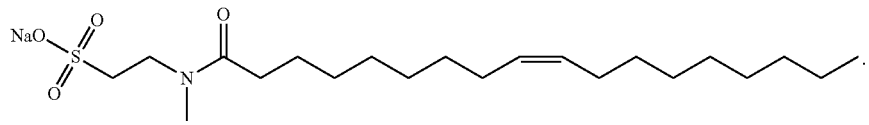

The aqueous clearance solution of the disclosure, in certain embodiments, comprises sodium methyl oleoyl taurate or a derivative thereof. In certain embodiments, the aqueous clearance solution of the disclosure comprises sodium methyl oleoyl taurate.

Other non-limiting examples of suitable N-methyltaurine derivatives and their salts include: methyl linoleoyl taurate having the structure

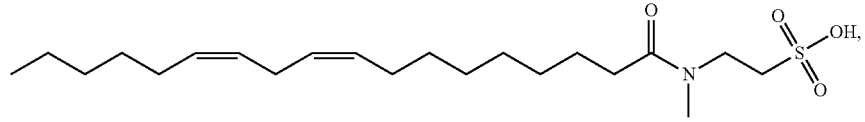 [SMILES: CCCCC/C=C\C/C=C\CCCCCCCC(=O)N(C)CCS(=O)(=O)O]

methyl linolenoyl taurate having the structure

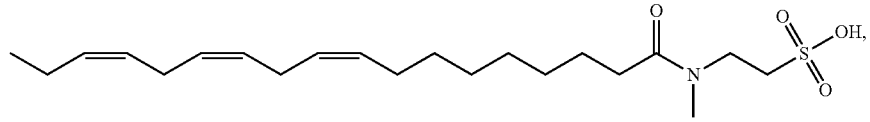 [SMILES: CC/C=C\C/C=C\C/C=C\CCCCCCCC(=O)N(C)CCS(=O)(=O)O]

methyl docosenoyl taurate having the structure

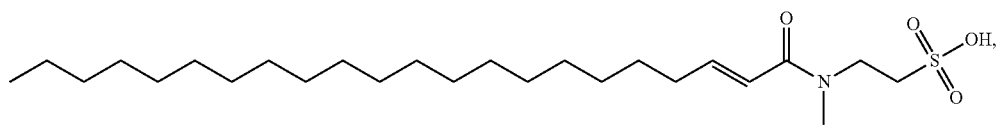 [SMILES: CCCCCCCCCCCCCCCCCCC/C=C/C(=O)N(C)CCS(=O)(=O)O]

methyl palmitoleoyl taurate having the structure

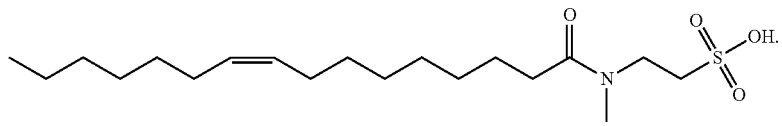 [SMILES: CCCCCC/C=C\CCCCCCCC(=O)N(C)CCS(=O)(=O)O]

In certain embodiments as otherwise described herein, the surfactant is selected from one or more of methyl oleoyl taurate, methyl linoleoyl taurate, methyl linolenoyl taurate, methyl docosenoyl taurate, methyl palmitoleoyl taurate, and salts thereof.

In certain embodiments, the aqueous clearance solution of the disclosure comprises one surfactant selected from methyl oleoyl taurate, methyl linoleoyl taurate, methyl linolenoyl taurate, methyl docosenoyl taurate, and methyl palmitoleoyl taurate, or a salt thereof.

In certain embodiments as otherwise described herein, the surfactant is a bile acid or a salt thereof. In certain embodiments, bile acids are selected from cholalic acid and its salts (cholates) (e.g., sodium cholate), deoxycholic acid and its salts (deoxycholates) (e.g., sodium deoxycholate), chenodeoxycholic acid and its salts (e.g., sodium chenodeoxycholate), lithocholic acid and its salts (e.g., sodium lithocholate), and ursodeoxycholic acid and its salts (e.g., sodium ursodeoxycholate).

The one or more surfactants may be present in the clearance solution described herein in a variety of amounts. In certain embodiments, the one or more surfactants is present in the clearance solution in a concentration in the range of about 0.0001% w/v to about 50% w/v, based on the total volume of the clearance solution. In certain embodiments, the one or more surfactants is present in a concentration in the range of about 0.001% w/v to about 50% w/v, for example, in the range of 0.001% w/v to 25% w/v, or 0.001% w/v to 10% w/v, or 0.001% w/v to 7% w/v, or 0.001% w/v to 5% w/v, or 0.001% w/v to 2% w/v, or 0.01% w/v to 1% w/v, or 0.001% w/v to 0.1% w/v, based on the total volume of the clearance solution. In certain embodiments, the one or more surfactants is present in a concentration in the range of about 0.01% w/v to about 50% w/v, for example, in the range of 0.01% w/v to about 25% w/v, or 0.01% w/v to about 10% w/v, or 0.01% w/v to 7% w/v, or 0.01% w/v to 5% w/v, or 0.01% w/v to 2% w/v, or 0.01% w/v to 1% w/v, or 0.01% w/v to 0.1% w/v, based on the total volume of the clearance solution. In certain embodiments, the one or more surfactants is present in a concentration in the range of about 0.5% w/v to about 50% w/v, for example, in the range of 0.5% w/v to 25% w/v, or 0.5% w/v to 10% w/v, or 0.5% w/v to 7% w/v, or 0.5% w/v to 5% w/v, or 0.5% w/v to 2% w/v, or 0.5% w/v to 1% w/v, based on the total volume of the clearance solution. In certain embodiments, the one or more surfactants is present in a concentration in the range of about 1% w/v to about 50% w/v, for example, in the range of 1% w/v to 25% w/v, or 1% w/v to 10% w/v, or 1% w/v to 7% w/v, or 1% w/v to 5% w/v, or 1% w/v to 2% w/v, based on the total volume of the clearance solution. In certain embodiments, the one or more surfactants is present in a concentration in the range of about 2% w/v to about 50% w/v, for example, in the range of 2% w/v to 25% w/v, or 2% w/v to 10% w/v, or 2% w/v to 7% w/v, or 2% w/v to 5% w/v, or 2% w/v to 3% w/v, based on the total volume of the clearance solution. In certain embodiments, the one or more surfactants is present in a concentration in the range of about 3% w/v to about 50% w/v, for example, in the range of 3% w/v to 25% w/v, or 3% w/v to 10% w/v, or 3% w/v to 7% w/v, or 3% w/v to 5% w/v, or 3% w/v to 4% w/v, based on the total volume of the clearance solution. In certain embodiments, the one or more surfactants is present in a concentration in the range of about 5% w/v to about 50% w/v, for example, in the range of 5% w/v to 25% w/v, or 5% w/v to 10% w/v, or 5% w/v to 7% w/v, or 7% w/v to 10% w/v, based on the total volume of the clearance solution. In certain embodiments, the one or more surfactants is present in a concentration in the range of about 10% w/v to about 50% w/v, for example, in the range of 20% w/v to 50% w/v, or 30% w/v to 50% w/v, or 40% w/v to 50% w/v, or 10% w/v to 30% w/v, or 20% w/v to 40% w/v, based on the total volume of the clearance solution.

Of course, the concentration of the one or more surfactants in the sample, e.g., after the biological sample and the clearance solution are combined is lower, than the concentration of surfactant in the clearance solution. Thus, in some embodiments, the one or more surfactants may be present in the sample in a concentration in the range of about 0.0003% w/v to about 10% w/v, based on the total combined volume of the biological sample and the clearance solution. For example, in certain embodiments, the one or more surfactants is present in a concentration in the range of about 0.001% w/v to about 10% w/v, or about 0.1% w/v to about 10% w/v, or about 0.5% w/v to about 10% w/v, or about 1% w/v to about 10% w/v, or about 0.001% w/v to about 1% w/v, or about 0.1% w/v to about 1% w/v, or about 0.5% w/v to about 1% w/v, or about 1% w/v to about 2% w/v, based on the total combined volume of the biological sample and the clearance solution. In certain embodiments, the one or more surfactants is present in a concentration in the range of about 0.001% w/v to about 3% w/v, or about 0.1% w/v to about 3% w/v, or about 0.5% w/v to about 3% w/v, or about 1% w/v to about 3% w/v, or about 0.001% w/v to about 1% w/v, or about 0.1% w/v to about 1% w/v, or about 0.5% w/v to about 1% w/v, or about 1% w/v to about 2% w/v, based on the total combined volume of the biological sample and the clearance solution. In some embodiments, the one or more surfactants may be present in the sample in a concentration in the range of about 0.0001% w/v to about 10% w/v, based on the total combined volume of the biological sample, the clearance solution, and the chelator solution. For example, in certain embodiments, the surfactant is present in a concentration in the range of about 0.0003% w/v to about 10% w/v, or about 0.001% w/v to about 10% w/v, or about 0.005% w/v to about 10% w/v, or about 0.1% w/v to about 10% w/v, or about 0.5% w/v to about 10% w/v, or about 1% w/v to about 10% w/v, based on the total combined volume of the biological sample, the clearance solution, and the chelator solution. in certain embodiments, the one or more surfactants is present in a concentration in the range of about 0.0003% w/v to about 3% w/v, or about 0.001% w/v to about 3% w/v, or about 0.005% w/v to about 3% w/v, or about 0.1% w/v to about 3% w/v, or about 0.5% w/v to about 3% w/v, or about 1% w/v to about 3% w/v, or about 0.001% w/v to about 1% w/v, or about 0.1% w/v to about 1% w/v, or about 0.5% w/v to about 1% w/v, or about 1% w/v to about 2% w/v, based on the total combined volume of the biological sample, the clearance solution, and the chelator solution.

The clearance solution may be acidic or basic. In certain embodiments, the clearance solution is acidic; e.g., having a pH of less than 7. For example, the clearance solution may have a pH of ≤6, e.g., a pH of about 3 to about 6, or about 4 to about 6, or about 5 to about 6. In certain embodiments, the clearance solution may have a pH of ≤5, e.g., a pH of about 3 to about 5, or about 4 to about 5, or about 3 to about 4. In certain embodiments, the clearance solution may even have a pH of ≤3, for example a pH of about 2 to about 3.

To obtain the clearance solution having the desired acidic pH, a buffer of suitable acidic pH may be included. Such buffer, for example, may include one or more acids. Thus, in certain embodiments, the clearance solution comprises an inorganic acid, such as phosphoric acid, or an organic acid. Suitable organic acids include, but are not limited to, formic acid, ascorbic acid, carbonic acid, carboxylic acids, citric acid, and acetic acid. In some embodiments, the organic acid is a weak acid. The pKa of acids suitable for use in the methods of invention may range from 2.0 to 6.4. In certain embodiments, the pKa is in the range of about 3.0 to 5.5, or about 3.0 to 6.0, or about 3 to 6.4. In certain embodiments, the pKa is in the range of about 2.0 to 4.0, or about 2.0 to 5.0, or about 2.0 to 5.5, or about 2.0 to 6.0. In certain embodiments, the pKa is in the range of about 4.0 to 5.0, or about 4.0 to 5.5, or about 4.0 to 6.0, or about 4.0 to 6.4. In certain embodiments, the clearance solution comprises carboxylic acid. In certain embodiments, the clearance solution comprises citric acid or acetic acid. In certain embodiments, the clearance solution comprises citric acid. In certain embodiments, the clearance solution may have chelating properties. For example, the citric acid may also act as a chelator during contacting of the sample with the clearance solution. In certain embodiments, the clearance solution may comprise a suitable chelating agent (i.e., in addition to the organic acid or instead of the organic acid). The examples of chelating agents are described below.

The concentration of the acid (e.g., organic acid) in the clearance solution may be selected to achieve the desired pH of the clearance solution. In certain embodiments, the concentration of the acid is in the range of about 50 mM to 5 M, for example, in the range of about 200 mM to 5 M, or 350 mM to 5 M, or 500 mM to 5 M. In certain embodiments, the concentration of the acid is in the range of about 50 mM to 1 M, for example, in the range of about 200 mM to 1 M, or 300 mM to 1 M, or 350 mM to 1 M, or 400 mM to 1 M, or 500 mM to 1 M. In certain embodiments, the concentration of the acid is in the range of about 350 mM to 1 M, for example, in the range of about 400 mM to 1 M, or 450 mM to 1 M, or 500 mM to 1 M, or 750 mM to 1 M. In certain embodiments, the concentration of the acid is in the range of about 300 mM to 500 mM, for example, in the range of about 320 mM to 500 mM, or 350 mM to 500 mM, or 370 mM to 500 mM. In certain embodiments, the concentration of the acid is in the range of about 300 mM to 370 mM, for example, in the range of about 320 mM to 370 mM, or 340 mM to 370 mM, or 350 mM to 370 mM, or 340 mM to 360 mM. In certain embodiments, the concentration of the acid is in the range of about 300 mM to 350 mM, for example, about 320 mM to 350 mM.

The concentration of the acid in the sample, e.g., after the biological sample and the clearance solution are combined, is lower than the concentration of the acid in the clearance solution. Thus, in some embodiments, acid may be present in the sample in a concentration in the range of about 5 mM to 250 mM, based on the total combined volume of the biological sample and the clearance solution. For example, the concentration of the acid is in the range of about 10 mM to 250 mM, or 50 mM to 250 mM, or 100 mM to 250 mM, or 150 mM to 250 mM, or 200 mM to 250 mM, based on the total combined volume of the biological sample and the clearance solution. In certain embodiments, the concentration of the acid is in the range of about 5 mM to 200 mM, for example, in the range of about 10 mM to 200 mM, or 50 mM to 200 mM, or 100 mM to 200 mM, or 150 mM to 200 mM, based on the total combined volume of the biological sample and the clearance solution. In certain embodiments, the concentration of the acid is in the range of about 10 mM to 150 mM, for example, in the range of about 50 mM to 150 mM, or 100 mM to 150 mM, based on the total combined volume of the biological sample and the clearance solution.

In certain embodiments, the clearance solution is basic; e.g., having a pH of more than 7. For example, the clearance solution may have a pH≤14, e.g., a pH of about 10 to about 14, or about 11 to about 14, or about 12 to about 14. In certain embodiments, the clearance solution may have a pH of ≥10, e.g., a pH of about 10 to about 11, or about 10 to about 12, or about 10 to about 13. To obtain such clearance solution having the desired basic pH, a buffer of suitable basic pH may be included. Suitable basic buffers and concentrations may be as described below with respect to the chelator solution.

In certain embodiments, the methods of the disclosure may further include contacting the sample with an aqueous chelator solution. In some embodiments, contacting with the chelator solution is performed after contacting with the clearance solution. In some embodiments, contacting with the chelator solution is performed before contacting with the clearance solution.

The chelator solution may comprise one or more chelating agents. The chelating agent is particularly useful for dissolving crystals, such as calcium and magnesium-containing crystals (oxalate and struvite) appearing in urine. Any kind of agent may be used as long as it is a decrystalizing agent. Some examples of the chelating agents include, but are not limited to ethylene glycol-bis(beta-aminoethyl ether)-N,N,N',N'-tetraacetic acid tetrasodium salt (EGTA), ethylenediaminetetraacetic acid tetrasodium salt dehydrate (EDTA), 1,2-cyclohexylenedinitrilotetraacetic acid (CDTA), dihydroxyethylglycine (DHEG), diaminohydroxypropanetetraacetic acid (DPTA-OH), ethylenediamine-N,N'-diacetic acid (EDDA), ethylenediamine-N,N'-di-3-propionate (EDDP), glycoletherdiamine-N,N,N',N'-tetraacetic acid (GEDTA), hydroxyethylethylenediaminetriacetic acid (HEDTA), lidofenin (HIDA), methyl-EDTA, trisodium nitrilotriacetate (NTA), pentetic acid, diethylenetriaminepentaacetic acid (DTPA), citric acid, sodium citrate, crown ethers, and the like. In certain embodiments, the chelator solution comprises ethylene glycol-bis(beta-aminoethyl ether)-N,N,N',N'-tetraacetic acid tetrasodium salt (EGTA), ethylenediaminetetraacetic acid tetrasodium salt dehydrate (EDTA), or a combination thereof.

The concentration of the one or more chelating agents in the chelator solution may be selected to achieve the desired chelating activity. In certain embodiments, the concentration of each chelating agent in the chelator solution is in the range of about 3 mM to 2 M, for example, in the range of about 10 mM to 2 M, or 50 mM to 2 M, or 100 mM to 2 M, or 300 mM to 2 M, or 500 mM to 2 M. In certain embodiments, the concentration of each chelating agent is in the range of about 1 M to 2 M, for example, in the range of about 1.2 M to 2 M, or 1.5 M to 2M, or 1.7 M to 2M. In certain embodiments, the concentration of each chelating agent is in the range of about 100 mM to 1 M, for example, in the range of about 200 mM to 1 M, or 300 mM to 1 M, or 350 mM to 1 M, or 400 mM to 1 M, or 500 mM to 1 M. In certain embodiments, the concentration of each chelating agent is in the range of about 100 mM to 500 mM, for example, in the range of about 200 mM to 500 mM, or about 300 mM to 500 mM, or about 400 mM to 500 mM. In certain embodiments, the concentration of each chelating agent in the chelator solution is in the range of about 200 mM to 370 mM, for example, in the range of about 250 mM to 370 mM, or about 300 mM to 370 mM, or about 350 mM to 370 mM, or about 340 mM to 360 mM. In certain embodiments, the concentration of each chelating agent in the chelator solution is in the range of about 300 mM to 350 mM, for example, about 320 mM to 350 mM. In certain embodiments, the total concentration of the one or more chelating agents in the chelator solution is in the range of about 1 mM to 3 M, for example, in the range of about 10 mM to 3 M, or 50 mM to 3 M, or 100 mM to 3 M, or 300 mM to 3 M, or 500 mM to 3 M. In certain embodiments, the total concentration of the one or more chelating agents 3 mM to 2 M, for example, in the range of about 10 mM to 2 M, or 50 mM to 2 M, or 100 mM to 2 M, or 300 mM to 2 M, or 500 mM to 2 M. In certain embodiments, the total concentration of the one or more chelating agents is in the range of about 1 M to 2 M, for example, in the range of about 1.2 M to 2 M, or 1.5 M to 2M, or 1.7 M to 2M. In certain embodiments, the total concentration of the one or more chelating agents is in the range of about 100 mM to 1 M, for example, in the range of about 200 mM to 1 M, or 300 mM to 1 M, or 350 mM to 1 M, or 400 mM to 1 M, or 500 mM to 1 M. In certain embodiments, the total concentration of the one or more chelating agents is in the range of about 100 mM to 500 mM, for example, in the range of about 200 mM to 500 mM, or about 300 mM to 500 mM, or about 400 mM to 500 mM.

The concentration of the one or more chelating agents in the sample, e.g., after the biological sample, the clearance solution, and the chelator solution are combined, is lower than the concentration of the one or more chelating agents in the chelator solution. Thus, in some embodiments, the one or more chelating agents may be present in the sample in a concentration in the range of about 2 mM to 500 mM, based on the total combined volume of the biological sample, the clearance solution, and the chelator solution, for example, in the range of 10 mM to 500 mM, or 50 mM to 500 mM, or 100 mM to 500 mM, or 150 mM to 500 mM, or 200 mM to 500 mM, or 300 mM to 500 mM, or 400 mM to 500 mM. In certain embodiments, the one or more chelating agents has a concentration in the range of about 20 mM to 100 mM, for example, in the range of 25 mM to 100 mM, or 50 mM to 100 mM, or 75 mM to 100 mM, based on the total combined volume of the biological sample, the clearance solution, and the chelator solution. In certain embodiments, the one or more chelating agents has a concentration in the range of about 15 mM to 200 mM, for example, in the range of 20 mM to 200 mM, or 50 mM to 200 mM, or 100 mM to 200 mM, or 150 mM to 200 mM, based on the total combined volume of the biological sample, the clearance solution, and the chelator solution.

The chelator solution may be acidic or basic. In certain embodiments, the chelator solution is basic; e.g., having a pH of more than 7. For example, the chelator solution may have a pH≤14, e.g., a pH of about 10 to about 14, or about 11 to about 14, or about 12 to about 14. In certain embodiments, the chelator solution may have a pH of ≥10, e.g., a pH of about 10 to about 11, or about 10 to about 12, or about 10 to about 13.

To obtain the chelator solution having the desired basic pH, a buffer of suitable basic pH may be included. Such buffer, for example, may include one or more bases. Suitable bases include, but are not limited to, sodium hydroxide, potassium hydroxide, calcium hydroxide, sodium carbonate, potassium carbonate, calcium carbonate, tris(hydroxymethyl)-aminomethane (TRIS), [tris(hydroxymethyl)methylamino]propanesulfonic acid (TAPS), 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), 3-(N-morpholino)propanesulfonic acid (MOPS), and the like. In certain embodiments, the chelator solution comprises a sodium hydroxide solution.

In certain embodiments, the chelator solution is acidic; e.g., having a pH of less than 7. For example, the chelator solution may have a pH of ≤6, e.g., a pH of about 3 to about 6, or about 4 to about 6, or about 5 to about 6. In certain embodiments, the chelator solution may have a pH of ≤5, e.g., a pH of about 3 to about 5, or about 4 to about 5, or about 3 to about 4. In certain embodiments, the chelator solution may even have a pH of ≤3. To obtain such chelator solution having the desired acidic pH, a buffer of suitable acidic pH may be included. Suitable acidic buffers and concentrations may be as described above with respect to the clearance solution.

The methods of the disclosure beneficially require less volume of sample than assay traditional methods for similar analytes. For instance, in certain embodiments of the methods of the disclosure, the sample volume is between about 10 µL and about 500 µL; for example, from about 10 µL to about 300 µL, or about 10 µL to about 200 µL, or about 10 µL to about 100 µL, or about 50 µL to about 300 µL, or about 50 µL to about 200 µL, or about 100 µL to about 500 µL, or about 100 µL to about 300 µL, or about 100 µL to about 200 µL.

The clearance solution of the disclosure may be added in a particular volume based on the desired applications. For example, in certain embodiments of the methods of the disclosure, the clearance solution volume is between about 1 µL and about 500 µL; for example, from about 1 µL to about 300 µL, or about 1 µL to about 200 µL, or about 1 µL to about 100 µL, or about 1 µL to about 50 µL, or about 50 µL to about 300 µL, or about 50 µL to about 200 µL, or about 100 µL to about 500 µL, or about 100 µL to about 300 µL, or about 100 µL to about 200 µL.

The chelator solution of the disclosure may be added in a particular volume based on the desired applications. For example, in certain embodiments of the methods of the disclosure, the chelator solution volume is between about 1 µL and about 500 µL; for example, from about 1 µL to about 300 µL, or about 1 µL to about 200 µL, or about 1 µL to about 100 µL, or about 1 µL to about 50 µL, or about 50 µL to about 300 µL, or about 50 µL to about 200 µL, or about 100 µL to about 500 µL, or about 100 µL to about 300 µL, or about 100 µL to about 200 µL.

In one example embodiment, the method of the disclosure as described herein includes: contacting the biological sample with an acidic aqueous clearance solution comprising one or more surfactants, followed by contacting the sample with a basic aqueous chelator solution comprising one or more chelating agents. In another example embodiment, such method as described herein further includes determining the amount of bacteria in the sample.

In one example embodiment, the method of the disclosure as described herein includes: contacting the biological sample with a basic aqueous chelator solution comprising one or more chelating agents followed by contacting the sample with an acidic aqueous clearance solution comprising one or more surfactants. In another example embodiment, such method as described herein further includes determining the amount of bacteria in the sample. In certain embodiments, the sample is centrifuged prior to determining the amount of the bacteria. In some embodiments, the centrifugation may be performed before or after addition of the clearance solution. In further embodiments, the centrifugation may be performed before or after addition of the chelator solution. In other embodiments, the sample is not centrifuged prior to determining the amount of the bacteria.

After the treatment with the clearance solution and chelator solution (if used) but prior to determining the amount of bacteria in the sample, the sample may be maintained undisturbed (i.e., incubated) for a period of time. Thus, in certain embodiments, the sample may be incubated for about 30 seconds to about 30 minutes. For example, the methods may include incubating the sample for about 30 seconds to about 20 minutes, or about 30 seconds to about 10 minutes, or about 30 seconds to about 5 minutes, or about 30 seconds to about 2 minutes, or about 1 minute to about 30 minutes, or about 1 minute to about 20 minutes, or about 1 minutes to about 15 minutes, or about 1 minute to about 10 minutes, or about 1 minute to about 5 minutes, or about 5 minutes to about 30 minutes, or about 5 minutes to about 20 minutes, or about 5 minutes to about 15 minutes, or about 5 minutes to about 10 minutes, or about 2 minutes to about 8 minutes, or about 3 minutes to about 7 minutes, or about 2 minutes to about 13 minutes, or about 3 minutes to about 12 minutes.

In certain embodiments, the methods of the disclosure may further include contacting the sample with a stain or dye for the bacteria. Some examples of the suitable stains and dyes include, but are not limited to, Wright stain (methylene blue optionally with eosin), crystal violet dye (e.g., with grams iodine and safranin), and antibodies tagged with fluorescent molecules. In some embodiments, the bacteria are premeabilized by prior to the contacting of the sample with a stain or dye. Of course, in certain embodiments, the amount of bacteria in the sample is determined without staining or dying the bacteria. In additional embodiments, the bacteria are not permeabilized.

The amount of bacteria may be determined by counting bacteria or by analyzing bacteria (e.g., for bacterial shape or size). Such methods may involve analysis of the sample image under a light microscope. In some embodiments, the sample may be applied to a microscope slide, a capillary or a cuvette, such as a SediVue® cuvette (IDEXX Laboratories Inc., Westbrook, Maine, U.S.A.) Numerous microscopy techniques may be used, such as bright-field, dark-field, and fluorescence microscopy. In some embodiments, counting may be performed manually (e.g., without the aid of computer imaging). For example, manual counting may be performed by a human viewing the sample directly through a microscope. Manual counting may involve counting the number of bacteria per grid area on a microscope slide or the like, and using this count to calculate the number of bacteria per volume unit of urine. In some embodiments, the bacteria may be analyzed under microscope to determine shape (e.g., coccus, including cocci such as diplococci and cocci chains, or rod) and/or determine size. In some embodiments, analyzing may be performed manually (e.g., without the aid of computer imaging). For example, manual analysis may be performed by a human viewing the sample directly through a microscope.

The amount of bacteria may also be determined by
generating an image of the contacted sample by a camera;
measuring a number of pixels that correlates to the bacteria in the image; and
correlating the number of pixels with a predetermined number of pixels to obtain the amount of bacteria in the sample.

In certain embodiments, the predetermined number of pixels may be obtained by independently performing an empirical experiment using a standard sample having a known amount of bacteria.

In some embodiments, an algorithm, program, or software may be used to quantify the amount of bacteria in a sample. In some embodiments, a computing device coupled to or in communication with the camera executes instructions (e.g., instructions stored in a memory of the computing device) in order to measure an amount of bacteria in the sample. Such instructions may be executed by a processor of the computing device in order to automate a portion of the measurement described above in relation to naked-eye techniques. For example, the instructions may be configured to measure the amount of bacteria in the sample by measuring or determining a number of pixels that correlates to the bacteria (e.g., corresponds to bacteria cells or an area of the image that consists of a bacteria cells) in an image of the sample. Additionally or alternatively, the instructions may cause the computing device to measure an amount of bacteria in the sample by measuring an area of an image of the sample that includes bacteria. Measuring the area that includes the bacteria may include determining a number of pixels of an image that relate to the bacteria. Differentiating the bacteria from the background of the image may include analyzing a numerical value associated with the pixels. For example, each pixel in an image could include a value corresponding to an amount of collected light, a level of intensity, brightness, coloration, greyscale, or another optical property of the pixel (e.g., a pixel in 8-bit image could be represented by a number between 0 and 255, where 0 corresponds to black and 0 corresponds to white). In a particular example, a threshold value could be set such that pixels with a value higher than the threshold are considered as comprising the bacteria, while those with a value lower than the threshold value are considered background. In such a case, determining a number of pixels that relate to the bacteria may include determining a number of pixels that are above or below some threshold value.

As described above, the methods as described herein are carried out on a biological sample to, for example, measure bacteria. In general, the methods of the disclosure allow for a portion of the bacteria in the biological sample to remain viable after carrying out the methods of the disclosure, e.g., after contact with the clearance solution, the chelator solution, or both. Thus, in certain embodiments, at least a portion of the bacteria in the sample remains viable after contact with the clearance solution, the chelator solution, or both. For example, in certain embodiments, at least 10% of the bacteria in the sample remains viable after carrying out the methods of the disclosure, e.g., 10%-100%, 10%-80%, 10%-50%, 25%-40%. In certain embodiments, at least 30% of the bacteria in the sample remains viable after carrying out the methods of the disclosure, e.g., 30%-100%, 30%-80%, or 30-60%. In certain embodiments, at least 50% of the bacteria in the sample remain viable after carrying out the methods of the disclosure, e.g., 50-100%, 50-85%, or 60-100%. In certain embodiments, essentially all of the bacteria (e.g., at least 95%, 98%, or even 100%) in the sample remains viable after carrying out the methods of the disclosure.

In certain embodiments, less than 10% of the bacteria in the biological sample remain viable after carrying out the methods of the disclosure; for example, less than 5%, or less than 1%, or essentially no bacteria remains viable after carrying out the methods of the disclosure.

In certain embodiments, the methods of the disclosure include first determining that the biological sample contains non-bacterial particulate matter that interferes with the analysis of for the bacteria, and then carrying out the methods as described herein (e.g., contacting the biological sample with the aqueous clearance solution, etc.). One of skill in the art recognizes that only a portion of the biological sample would be used in the first determination and that a different portion of the biological sample would be contacted with the aqueous clearance solution. Therefore, in certain embodiments, the methods of the disclosure further include, prior to contacting the sample with the clearance solution: withdrawing a portion of the biological sample, analyzing the portion for bacteria; and determining that the presence or amount of non-bacterial particulate matter interferes with the analysis for bacteria.

In certain embodiments, the disclosure provides methods for measuring bacteria in a biological sample, including:
  analyzing a first portion of the biological sample for the bacteria in the first portion;
  determining that the presence or amount of non-bacterial particulate matter interferes with the analysis for the bacteria;
  contacting a second portion of the biological sample with the aqueous clearance solution as described herein; and
  determining the bacteria in the second portion to measure bacteria in the biological sample.

In some embodiments, the methods of the disclosure may further include making a determination about a health state of the patient based on at least the determined concentration of bacteria in the sample. In some cases, a computing device (e.g., a computer, a server, a processor, or a controller) in communication with the camera may use the determined concentration of bacteria to determine a health state, diagnose a disease (such as an infection), express a risk factor, or offer some other information about the health of a patient. In some embodiments, diagnosing a health state (e.g., a bacterial infection) may include determining whether the amount of bacteria is above or below a threshold value. Other health states and analyses are envisioned by one of ordinary skill in the art. Commonly, the health state is a urinary tract infection.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, "patient" refers to a warm blooded animal such as a mammal, preferably a human, cat, dog, rodent, primate, or horse. Patients may be healthy, or suffer from or have a potential to be afflicted with one or more diseases and disorders described herein. In some embodiments, the biological samples of the disclosure may be obtained or derived from patients.

As used herein, "salt' includes acid addition salts of compounds of the present disclosure. The salts may include cations based on the alkali and alkaline earth metals, such as sodium, lithium, potassium, calcium, magnesium, and the like, as well as ammonium, quaternary ammonium, and amine cations including, but not limited to ammonium, tetramethylammonium, tetraethylammonium, methylamine, dimethylamine, trimethylamine, triethylamine, ethylamine, and the like.

EXAMPLES

The methods of the disclosure are illustrated further by the following examples, which are not to be construed as limiting the disclosure in scope or spirit to the specific procedures and materials described in them.

Example 1

Fresh, refrigerated urine was stored at 2-8° C. until shortly before analysis. The sample was allowed to warm to room temperature (approximately 25° C.) prior to analysis. Analysis should be performed as soon as possible following receipt of the sample (e.g., within 12 hours).

Clearance solution was prepared by dissolving 875 mg of sodium methyl oleoyl taurate (available as Geropon T77 from Solvay, CAS RN 137-20-2) in 25 mL of 350 mM citric acid. Chelator solution was made to have 325 mM ethylenediaminetetraacetic acid tetrasodium salt dehydrate (EDTA, available from Sigma; CAS: 10378-23-1), 325 mM ethylene glycol-bis(beta-aminoethyl ether)-N,N,N',N'-tetraacetic acid tetrasodium salt (EGTA, available from Sigma; CAS RN: 13368-13-3) in 500 mM sodium hydroxide.

Samples that are sufficiently crowded to make it difficult to identify bacteria and samples having small debris that is difficult to distinguish from bacteria are particularly well suited for this procedure.

In particular, 60 μL of well-mixed, unspun urine sample was placed into the appropriate flat bottom microtiter well. Then, 15 μL of clearance solution was added into the well and mixed gently by pipetting up and down 5 times, taking care not to introduce unnecessary bubbles. 15 μL of chelator solution was then added and mixed gently by pipetting up and down 5 times, taking care not to introduce unnecessary bubbles. The sample was then let to settle for 5-10 minutes undisturbed. An inverted light microscope with phase contrast filter, 10×, and 40× objectives was used to determine the amount of bacteria.

Figure 2:
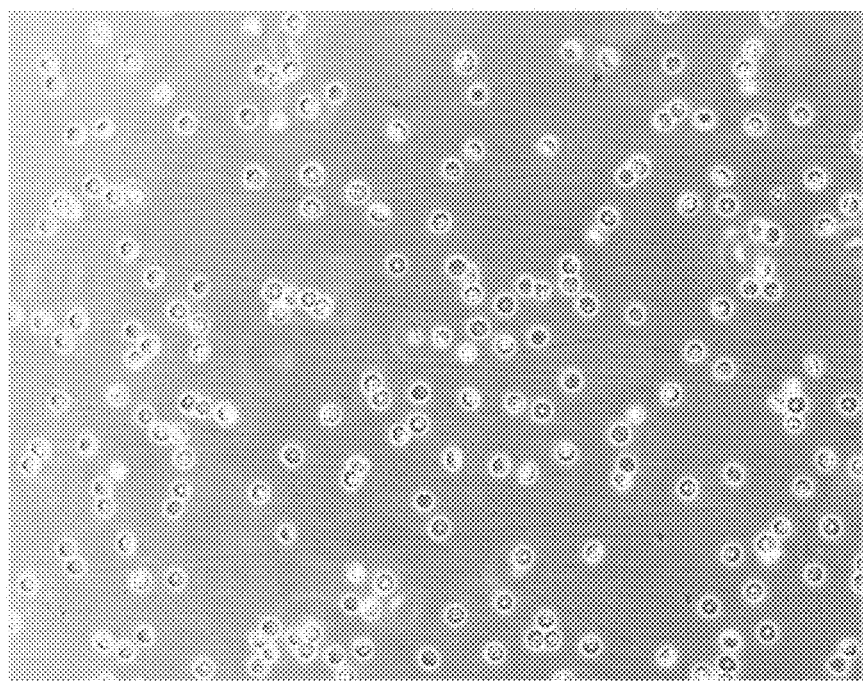
FIG. 2 illustrates the treatment of blood-spiked canine urine according to the methods of the disclosure. Panel A is the image of the before-treatment sample; and Panel B is the image after the treatment by the method disclosed in Example 1.
Figure 2:
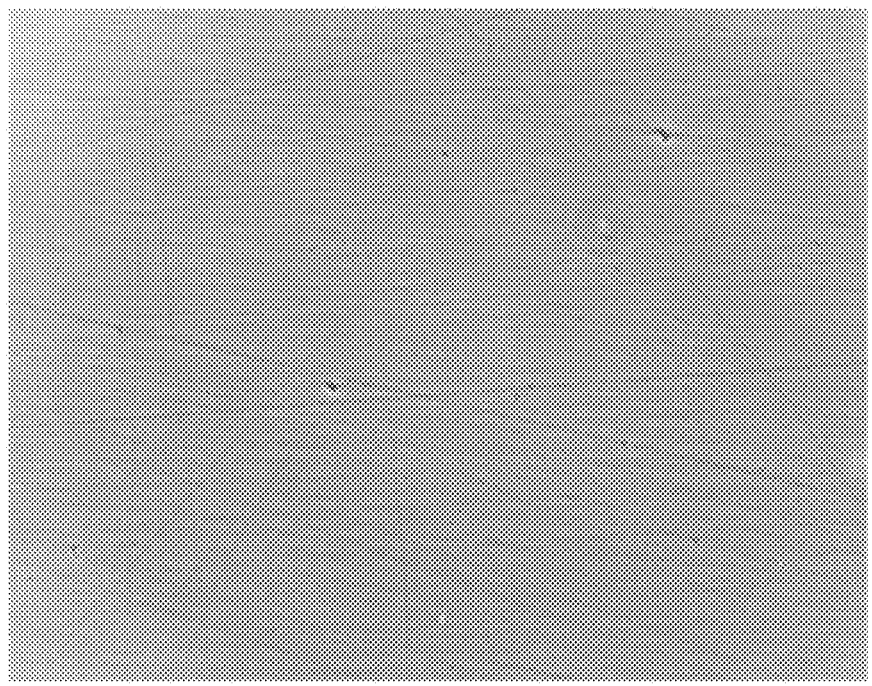

Blood-containing canine urine was treated using the materials and procedure described above. As provided in FIG. 2A, the before-treatment sample contained a significant amount of blood cells and other contaminants. After treatment, the sample was optically clear of the blood cells and other contaminants (FIG. 2B).

Example 2

Canine whole blood and/or *E. coli* grown in LB broth were added to a medium of 0.2 μm filtered canine urine (referred to herein as urine filtrate). The dilutions were 60× of a 4 hour *E. coli* culture. For the blood sample, the total dilution was about 1200×. Water was used as a dilution control and added at ratio of 1:9 to urine filtrate. Water was selected as a control because both clearance and chelator solutions are aqueous. The clearance and chelator solutions are prepared according to Example 1, and the same procedure was followed.

Figure 3:
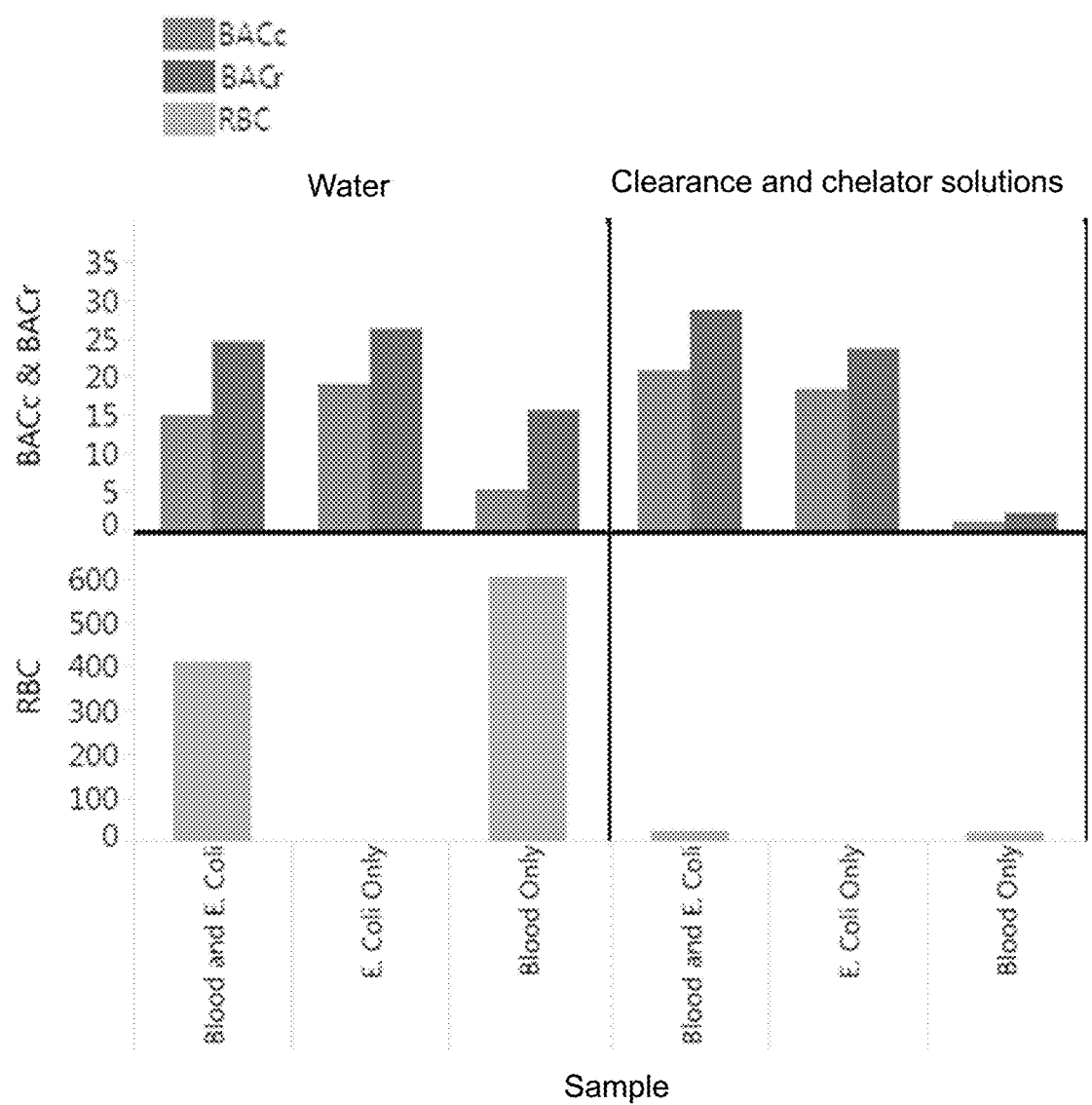
FIG. 3 illustrates the treatment of canine whole blood and/or *E. coli* samples according to the methods of Example 2. Water treatment is used a control. RBC is red blood cell count. BACc and BACr are bacteria-coccus cell count and bacteria-rod cell count, respectively.
Figure 4:
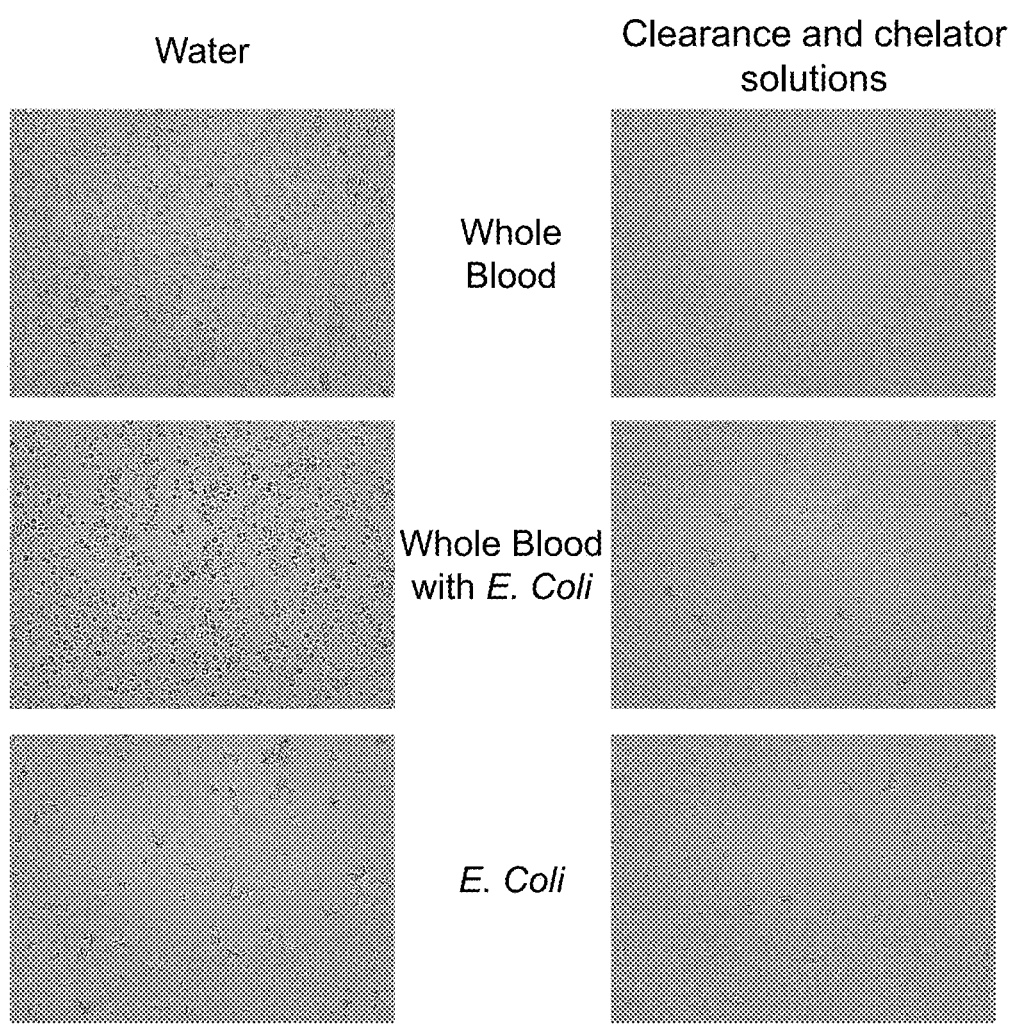
FIG. 4 illustrates the treatment of canine whole blood and/or *E. coli* samples according to the methods of Example 2.

As provided in FIG. 3, the method of the disclosure disrupts the blood cell membranes, while leaving the bacteria intact. Here the treatment with the method of the disclosure showed absence of bacteria in blood only sample, and presence of bacteria in the samples with *E. coli*. The water control showed the presence of bacteria even in blood only sample (i.e., was a false positive result). The images of the results are provided in FIG. 4.

Example 3

Figure 5:
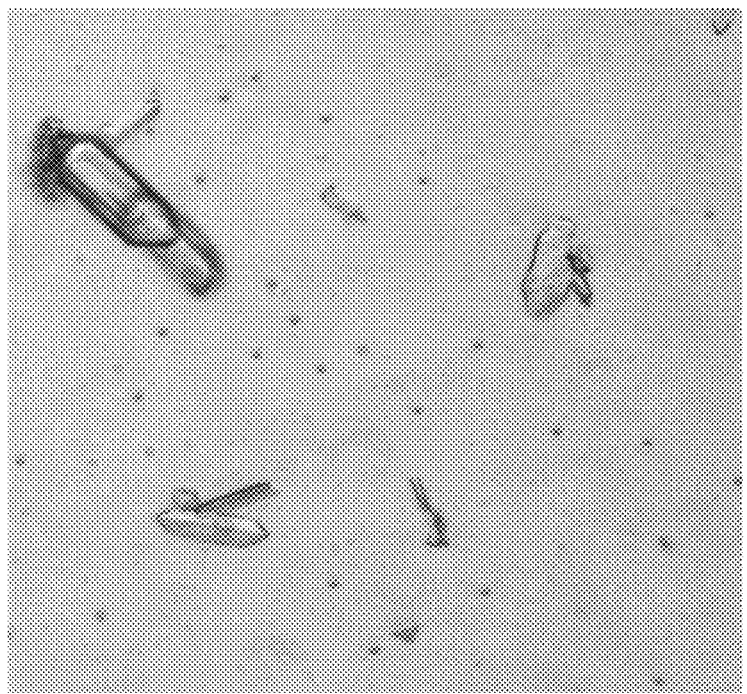
FIG. 5 provides the image of the urine sample treated by the method of the disclosure. Panel A is an image of canine urine and urine sediment under 10× optical magnification. Urine contains large crystalline debris as well as numerous blood cells. Panel B is an image of urine and urine sediment under 10× optical magnification after treatment with the method of the disclosure.
Figure 5:
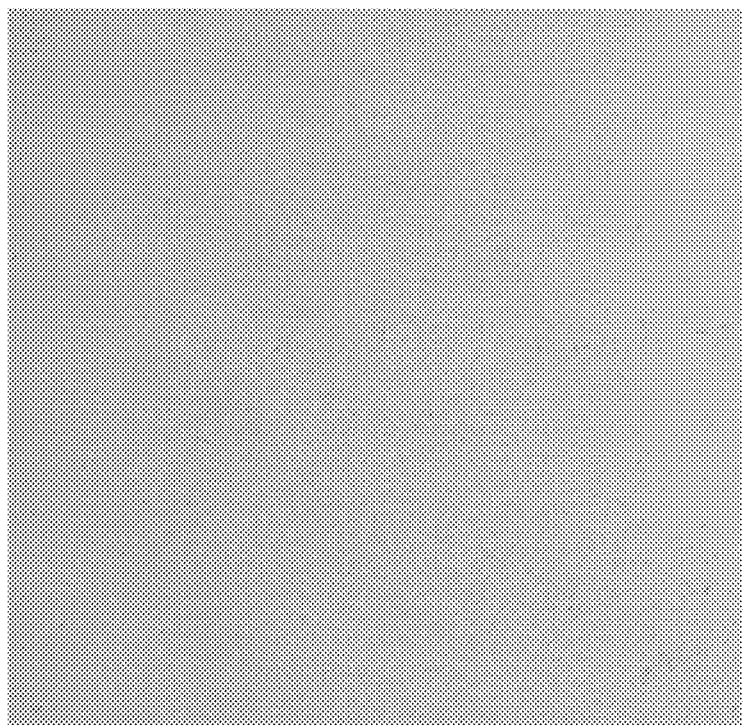

Canine urine containing large crystalline debris as well as numerous blood cells and bacteria was combined 19:1 with a 10% w/v solution of SMOT and mixed (i.e., the final concentration of SMOT was 0.5%). The resulting mixture was combined 19:1 with a solution containing 500 mM EDTA and 500 mM EGTA (i.e., the final concentration was 25 mM of each chelator) and mixed gently to produce the treated sample. The untreated urine and the treated sample were observed and photographed with a custom semi-automated microscope system. The exemplary images of the results are provided FIG. 5. The method of the disclosure (i.e., treatment with SMOT and chelating solution) cleared the urine of the crystalline debris and the blood cells, but the bacteria remained visible.

Example 4

Three test biological samples were prepared as follows. "Blood" sample was prepared by adding 5 μL of canine whole blood into 3 mL of filtered sterile canine urine; "*E. coli*" sample was prepared by adding 50 μL of lysogeny broth (LB) containing a 4-hour *E. coli* culture into 3 mL of filtered sterile canine urine; and "Blood and *E. coli*" sample was prepared by adding 5 μL of canine whole blood and 50 μL of LB containing a 4-hour *E. coli* culture into 3 mL of filtered sterile canine urine.

A 10% w/v solution of SMOT and a 10% w/v solution of sodium cholate in water (CAS: 361-09-1) were also prepared in water. 100 μL of SMOT solution, 100 μL of cholate solution, or 100 μL of plain water were added to 900 μL of each of the three test biological samples to obtain the treated sample. Then, 165 μL of the treated sample was transferred into the SediVue® cartridge for analysis on SediVue Dx® Urine Sediment Analyzer (available from IDEXX Laboratories, Inc., Westbrook, Maine).

Figure 6:
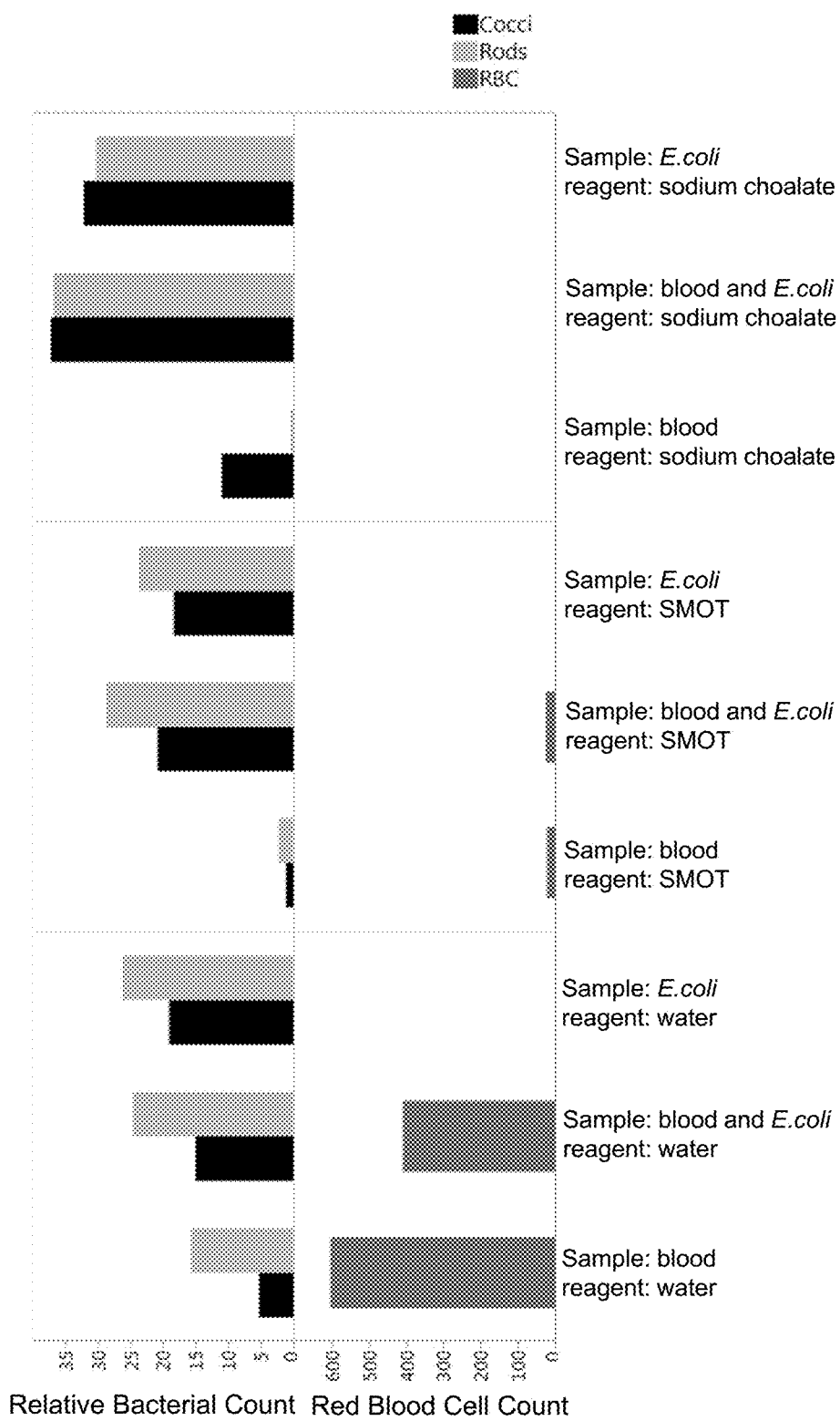
FIG. 6 illustrates treatment of canine urine with or without whole blood and/or *E. coli* according to one embodiment of the methods of the disclosure.

The results are shown in FIG. 6. The left-hand side panels of the graph show the number of bacteria (cocci and rods) as measured by the instrument, with the x-axis representing the average number of bacteria per high power field. The right-hand side panels of the graph show the number of red blood cells (RBC) measured by the instrument, with the x-axis representing the relative abundance of RBCs. In the control samples (water), the instrument reported bacteria in the blood-containing urine sample. Thus, the RBC led to false positive bacterial counts. After treatment of the samples with either SMOT or sodium cholate, the blood-containing urine sample had significantly reduced overall bacteria counts as compared to water-treated samples. Therefore, treatment method of the disclosure on a urine sample with SMOT or sodium cholate is effective in clearing RBCs and improves the accuracy of bacterial counting.

Example 5

SMOT was saturated to obtain sodium methyl stearoyl taurate (i.e., 2-[methyl(octadecanoyl)amino]ethanesulfonate sodium salt or SMST), as follows. 500 mg of sodium-N-methyl-N-oleyl taurate (1.2 mmol), ammonium formate (884 mg, 12 mmol, 10 eq), and 10% Pd/C (380 mg, 0.3 mmol) was suspended in methanol (30 mL), under inert atmosphere (Argon). The reaction mixture was stirred under inert atmosphere at room temperature overnight. The mixture was filtered through celite, and the celite was washed with 3×20 mL ethyl acetate. The combined organics removed under rotary evaporation to provide the product (Sodium-N-Methyl-N-Stearoyl Taurate) as a yellowish oil. SMOT clearance solution was prepared to have 3.5% w/v SMOT in 350 mM citric acid; SMST clearance solution was prepared to have 2.2% w/v SMST in 350 mM citric acid; and chelating solution was prepared to have 325 mM EDTA, 325 mM EGTA in 500 mM NaOH. A canine urine sample (60 μL) was first treated with 15 μL of a clearance solution (i.e., SMOT or SMST). The concentration of SMOT in SMOT-treated sample was 0.7% w/v, whereas the concentration of SMST in SMST-treated sample was 0.44% w/v. Following treatment of the urine sample with the clearance solution, 15 μL of chelating solution was added. The treated sample was transferred into the SediVue® cartridge for analysis on SediVue Dx® Urine Sediment Analyzer.

Figure 7:
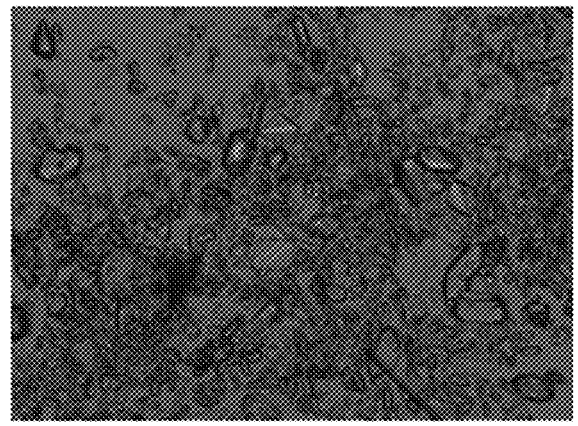
FIG. 7 illustrates treatment of canine urine samples according to one embodiment of the methods of the disclosure.
Figure 7:
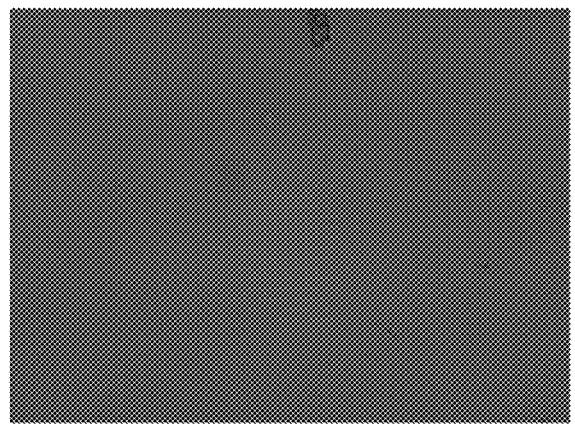
Figure 7:
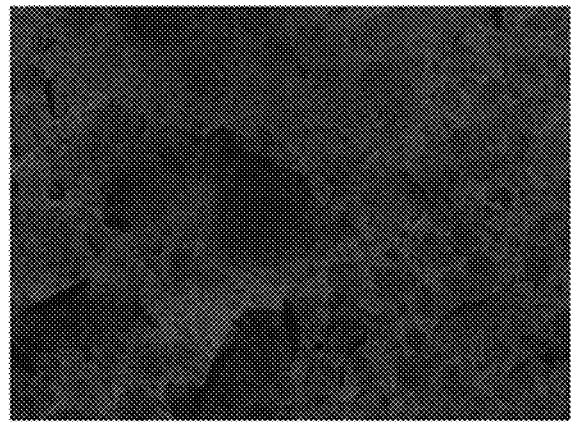

As provided in FIG. 7, treatment method of the disclosure with SMOT resulted in optical clearing of the sample. Treatment with SMST, however, did not yield optical clearing of the sample.

Comparative Example 6

Six different chelator solutions were prepared: 200 mM EDTA solution; 200 mM EGTA solution; 1M EDTA solution; 1M EGTA solution; 100 mM/100 mM EDTA/EGTA; and 500 mM/500 mM EDTA/EGTA.

Each chelator solution (5 μL) was individually added to 195 μL of canine urine containing crystals. Thus, the final concentrations of the treated samples were: 5 mM EDTA; 5 mM EGTA; 25 mM EDTA; 25 mM EGTA; 2.5 mM/2.5 mM EDTA/EGTA; and 12.5 mM/12.5 mM EDTA/EGTA. 165 μL of the treated sample was then added to a SediVue® cartridge for analysis on SediVue Analyzer. Here, the number of calcium oxalate crystals and magnesium ammonium phosphate (struvite) crystals per HPF (high power field) was assessed.

Figure 8A:
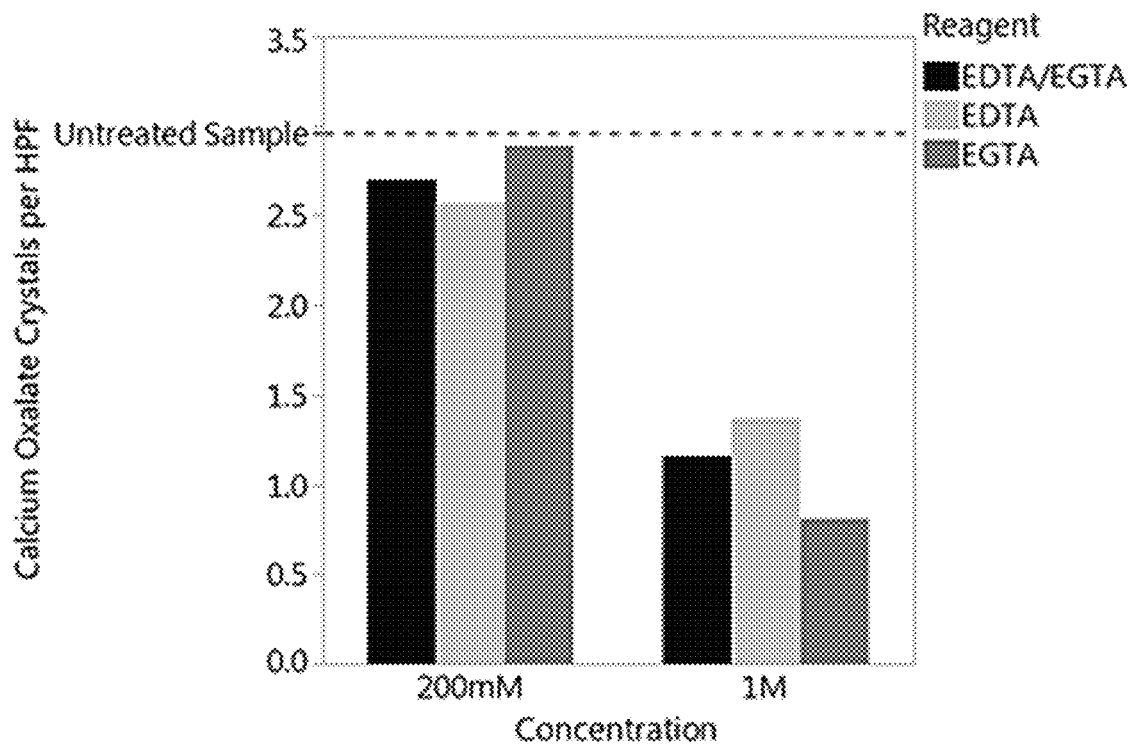
FIG. 8A shows the automated crystal counts of urine sample treated with different chelator solutions.
Figure 8A:
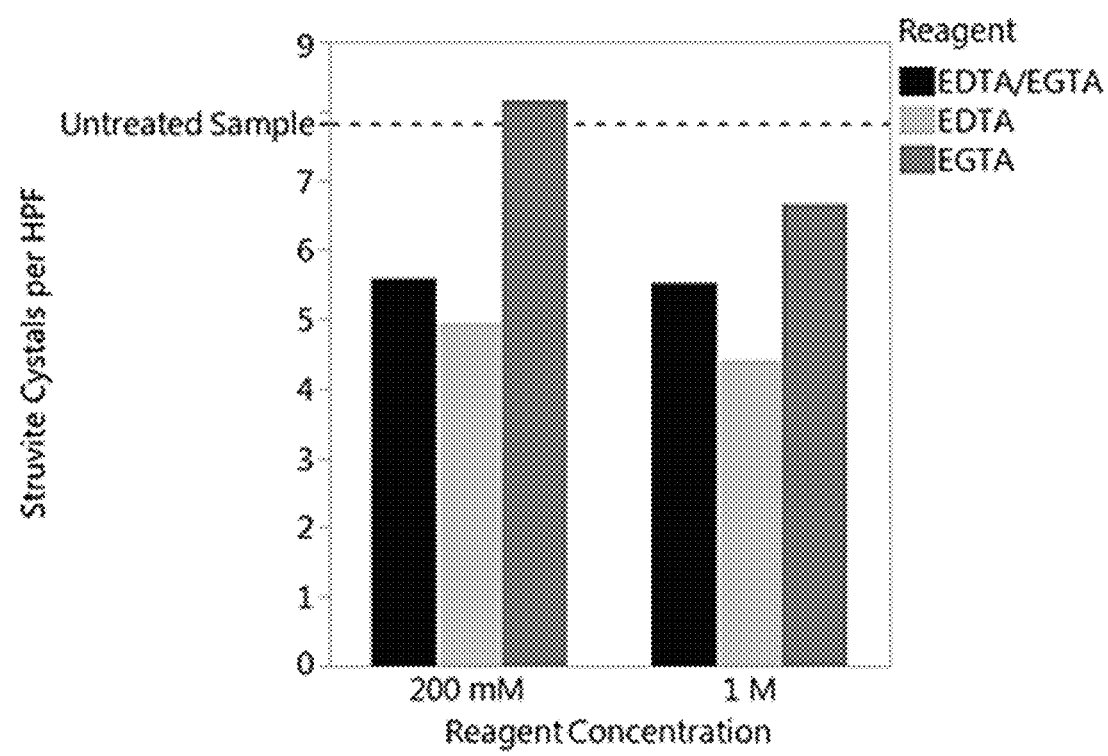

The results of the automated crystal counts after the treatment of the crystal-containing urine sample with chelator solutions is provided in FIG. 8A. Treatment with each chelator solution resulted in a reduction of both calcium oxalate and struvite crystal counts with greater reduction in crystal counts at higher chelating agent concentrations.

Figure 8B:
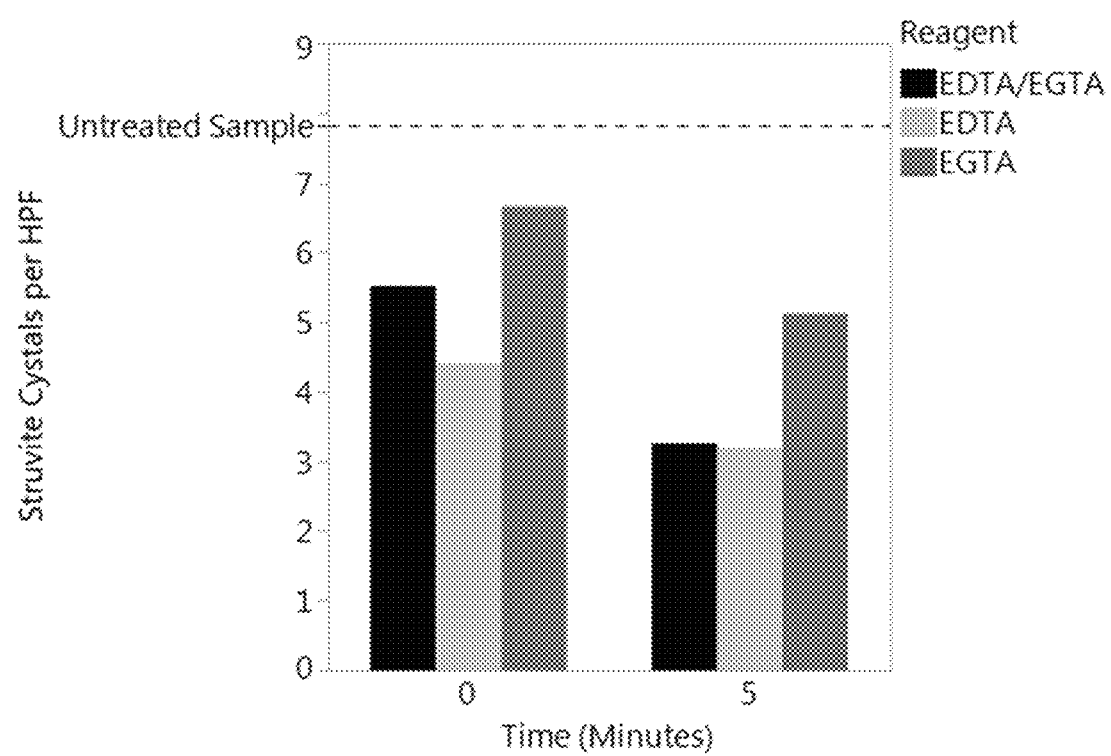
FIG. 8B shows the effects of a 5-minute incubation of the treated sample prior to analysis on the crystal count. The dashed lines represent the crystal counts in the urine sample prior to the chelator solution treatments. Reagent concentrations shown are of the chelator solutions prior to addition to the urine sample. HPF=High power field.

In order to determine the effect of incubation time on crystal counts, 5 μL of chelator solution (1M EDTA; 1M EGTA; or 500 mM EDTA and 500 mM EGTA) was individually added to 195 μL of canine urine containing crystals and allowed to incubate for 5 minutes prior to analysis on the instrument. The results of struvite crystal count determination are shown in FIG. 8B. Treatment with each chelator solution followed by a 5-minute incubation period resulted in a further reduction of the struvite crystal count.

Example 7

200 μL aliquots of 10% w/v SMOT was combined with varying amounts (from 0.2 μL to 6.4 μL) of 4 M citric acid or 4 M acetic acid to generate clearance solutions of different acidity. 16.5 μL of each clearance solution was added with gentle mixing to 165 μL of canine urine having crystalline debris and bacteria. The pH of the resulting solution was measured, and 165 μL of this solution was transferred to a SediVue® cartridge and the total crystal count (CRY) was measured using SediVue Analyzer.

Figure 9A:
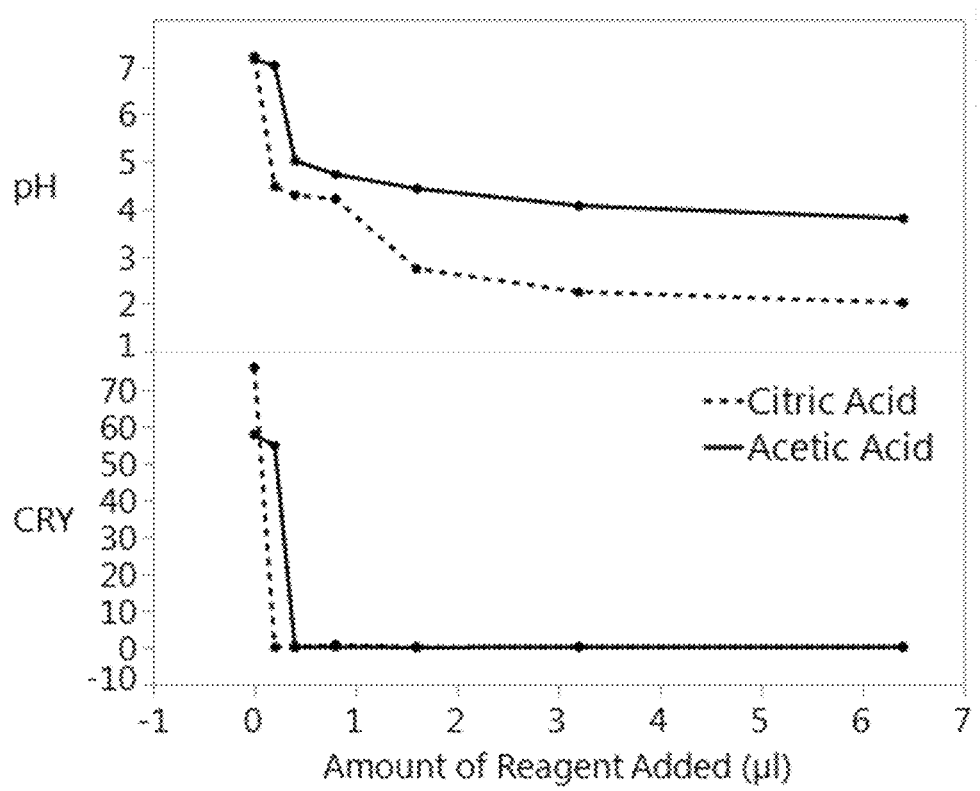
FIG. 9A shows pH values and the total crystals count (CRY) results of treatment of canine urine sample having crystalline debris and bacteria according to one embodiment of the methods of the disclosure.
Figure 9B:
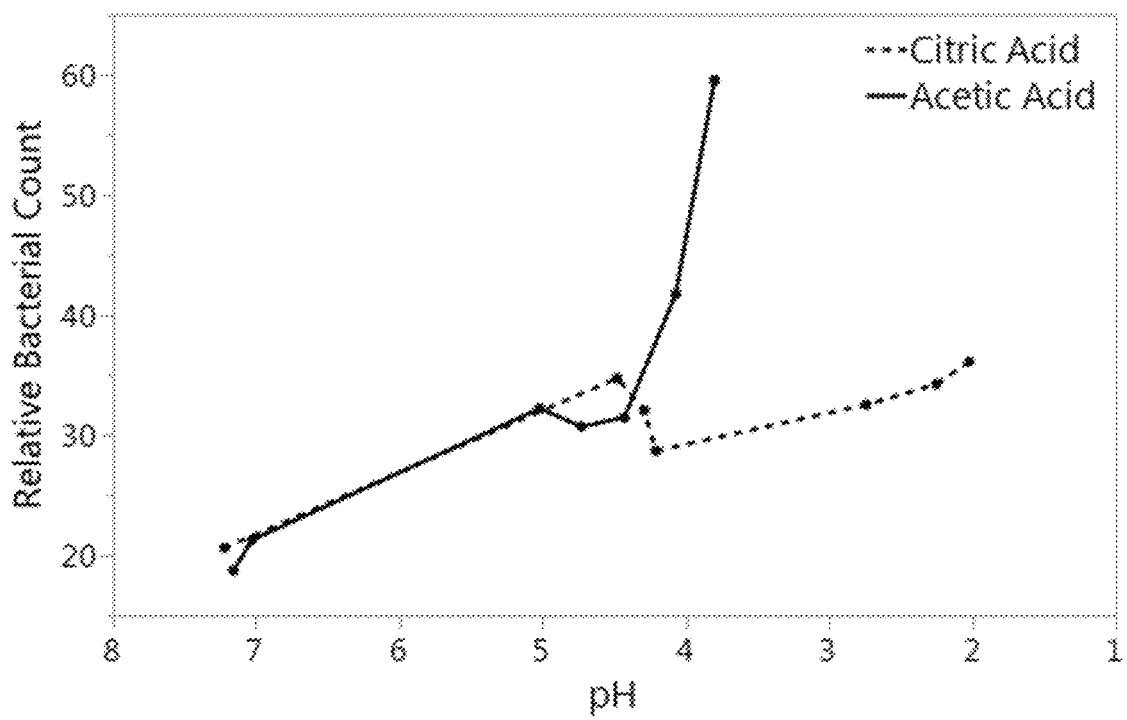
FIG. 9B shows relative bacterial count after treatment of canine urine sample having crystalline debris and bacteria according to one embodiment of the methods of the disclosure.

The pH values and the total crystals count (CRY) are plotted against increasing amounts of acids, and these results are provided in FIG. 9A. Addition of either citric acid or acetic acid resulted in a reduction of the CRY count. The CRY counts dropped to zero with the addition of at least 0.2 μL of citric acid (having final pH of 4.5), or with the addition of at least 0.4 μL of acetic acid (having final pH of 5.0). But as shown in FIG. 9B, acetic acid resulted in a sharp increase in bacterial count at pH values below 4.5, suggesting that treatment with acetic acid results in features that are falsely counted as bacteria. Thus, in certain embodiments, citric acid may be used in the clearance solution at a wide range of pH values. In certain embodiments, acetic acid may be used in the clearance solution at pH of ≥4.5.

Example 8

165 μL canine urine having crystalline debris (mostly struvites) was treated with 16.5 μL of a series of clearance solutions containing 10 w/v % SMOT and ranging from 154 mM to 1 M citric acid, followed by gentle mixing. 165 μL of this mixture was then combined with 16.5 μL of water and gently mixed. 165 μL of the resulting mixture was then placed into a SediVue® cartridge and the total crystal count was measured using SediVue Analyzer. As provided in Table 1, the total crystal count per high power field decreased with increasing concentrations of citric acid in the clearance solution.

TABLE 1

| Starting SMOT concentration (% w/v) | Starting citric acid concentration (mM) | Total crystal count/HPF |
|---|---|---|
| 0 | 0 | 44.0 |
| 10 | 154 | 22.3 |
| 10 | 364 | 19.2 |
| 10 | 500 | 18.4 |
| 10 | 1000 | 15.0 |

Next, the effect of the pH on the chelator solution on total crystal count was examined. 165 μL of the canine urine was combined with 16.5 μL of water, or with 16.5 μL of a clearance solution containing 10% w/v SMOT in 1M citric acid, followed by gentle mixing. 165 μL of this mixture was then combined with 16.5 μL of a series of chelator solutions containing 500 mM EDTA, 500 mM EGTA, and NaOH (0 mM, 500 mM or 2000 mM), and mixed gently. 165 μL of the resulting mixture was then placed into a SediVue® cartridge and the total crystal count was measured using SediVue Analyzer. As provided in Table 2, the total crystal count per high power field decreased with the addition of EDTA and EGTA. The total crystal count further decreased with increasing concentrations of NaOH (i.e., increasing pH) in the clearance solution.

TABLE 2

| Chelator solution | Total crystal count/HPF |
|---|---|
| water | 15.0 |
| 500 mM EDTA/500 mM EGTA | 6.0 |
| 500 mM EDTA/500 mM EGTA/500 mM NaOH | 7.6 |
| 500 mM EDTA/500 mM EGTA/2M NaOH | 3.3 |

Example 9

165 μL canine urine containing urinary crystals, bacteria, and 0.1% v/v of canine blood was combined with 16.5 μL of clearance solution (10% w/v SMOT in 1M citric acid) and mixed gently. The final concentration of SMOT in the treated urine sample was 0.9% w/v and citric acid was 91 mM. Then, to 165 μL of this mixture 16.5 μL of chelator solution (500 mM EGTA, 500 mM EDTA, 2M NaOH) was added and mixed gently. The final concentration of EGTA and EDTA after the addition was 45 mM each and NaOH was 182 mM. 165 μL of the resulting mixture was then placed into a SediVue® cartridge and analyzed using SediVue Analyzer, either immediately or after a 4-minute incubation. The negative control was the untreated canine urine containing urinary crystals, bacteria, and 0.1% v/v of canine blood.

Figure 10A:
FIG. 10A illustrates treatment of canine urine samples according to two different embodiments of the methods of the disclosure.
Figure 10A:
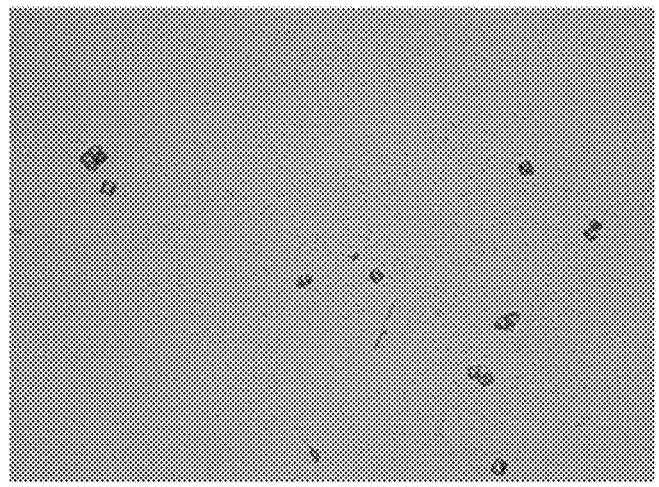
Figure 10A:
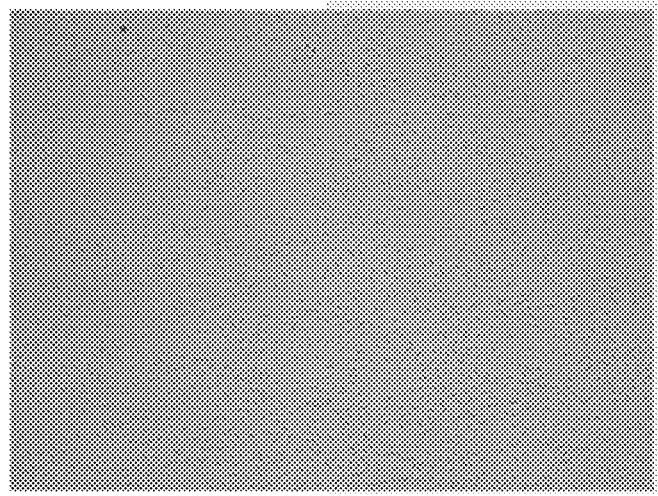

FIG. 10A shows microscopic images of the urine without treatment, with treatment and immediate analysis, and with treatment after a 4-minute incubation. With immediate analysis, the vast majority of red blood cells (RBCs) and crystals had been cleared from the sample, but the bacteria remained visible. The four minute incubation yielded a further improvement in the clearing of the sample from crystals and cells debris, but the bacteria remained visible. For example, the number of RBCs per high power field, as counted by the instrument (without the 4-minute incubation), was 6.30 in the untreated sample and 1.84 in the treated sample. Thus, the treatment method of the disclosure yielded a reduction in RBC count of 71%. The number of total crystals per high power field (without the 4-minute incubation), as counted by the instrument, was 2.88 in the untreated sample and 0.31 in the treated sample. Thus, the treatment method of the disclosure yielded a reduction in total crystal count of 89%.

Figure 10B:
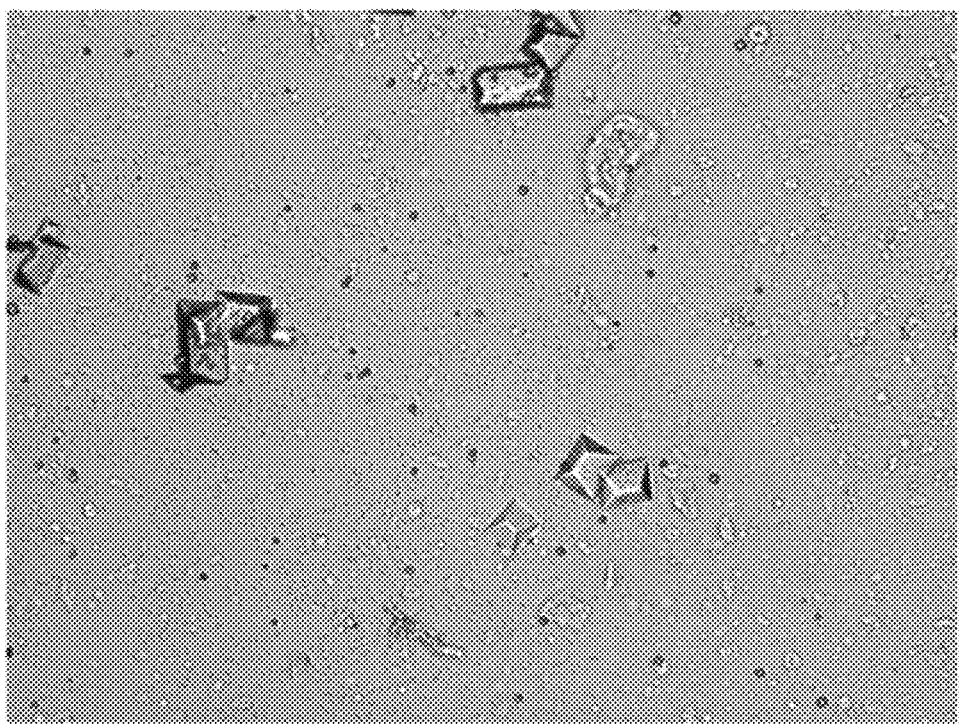
FIG. 10B illustrates treatment of highly crystallized canine urine sample according to one embodiment of the methods of the disclosure.
Figure 10B:

Next, 165 μL of highly crystallized canine urine known to contain bacteria was treated with 16.5 μL of clearance solution as described above and mixed gently. To 165 μL of this mixture, 16.5 μL of chelator solution as described above was added and mixed gently. An aliquot of the treated final sample was compared with the untreated highly crystallized canine urine using light microscopy. As shown in FIG. 10B, the urinary crystals and the bacteria were visible in the untreated urine. Only the bacteria, but not the crystals, were visible in the treated urine. Thus, the treatment method of the disclosure was able to dissolve the crystals in the highly crystallized samples. The treatment method cleared the urine of the crystals as determined by light microscopy, and maintained the bacteria intact and, for example, available for further analysis.

Another experiment was carried out as described above on 165 μL of canine urine containing mucus, cellular debris, and bacteria. Clearance solution and chelator solution were as described above. An aliquot of the treated sample was compared to the untreated urine by light microscopy. The mucus, cellular debris, and bacteria (including cocci chains) were visible in the untreated urine. In the treated urine, the bacteria, including cocci chains, were visible; the mucus and cellular debris were not visible. Thus, the treatment method of the disclosure cleared the urine of the mucus and cellular debris as determined by light microscopy, and maintained the bacteria intact (including undisrupted cocci chains).

Finally, the performance of bacterial recognition by the instrument before and after treatment was compared to quantitative culture. 162 fresh urine samples known to contain bacteria were used in this experiment. For quantitative culture, the urine samples were diluted and plated onto blood agar plates according to procedures well-known in the art. For example, the urine samples were diluted 1:49, and 50 µL of the dilution was plated onto blood agar. Following overnight incubation, the number of colonies was counted and the titer of bacteria per milliliter urine was calculated. Samples were then grouped into positive/negative bins according to three thresholds: $10^6$ cells/mL, $10^5$ cells/mL, and $10^4$ cells/mL. For example, at a threshold of $10^6$ cells/mL, urine samples with $10^6$ bacteria/mL or above were deemed positive, and urine samples with less than $10^6$ bacteria/mL were deemed negative. For determination on the SediVue Analyzer, 165 µL of urine sample was combined with 16.5 µL of clearance solution as described above and mixed gently. To 165 µL of this mixture, 16.5 µL of chelator solution as described above was added and mixed gently. 165 µL of the resulting mixture was then placed into a SediVue® cartridge and analyzed using SediVue Analyzer. The Analyzer returned "positive" or "negative" calls. The results are provided in Table 3.

TABLE 3

|  | call | culture (bacteria/mL) | | | | | | | |
|---|---|---|---|---|---|---|---|---|---|
|  |  | $10^6$ | | | $10^5$ | | | $10^4$ | | |
|  |  | − | + | % | − | + | % | − | + | % |
| untreated | − | 85 | 14 | A = 77 | 73 | 26 | A = 77 | 59 | 40 | A = 71 |
|  | + | 23 | 40 | Se = 74 | 11 | 52 | Se = 67 | 7 | 56 | Se = 58 |
|  |  |  |  | Sp = 79 |  |  | Sp = 88 |  |  | Sp = 89 |
| treated | − | 79 | 2 | A = 80 | 72 | 9 | A = 87 | 55 | 26 | A = 77 |
|  | + | 29 | 52 | Se = 96 | 12 | 69 | Se = 88 | 11 | 70 | Se = 73 |
|  |  |  |  | Sp = 73 |  |  | Sp = 86 |  |  | Sp = 83 |

"A" is accuracy; "Se" is sensitivity; "Sp" is specificity.

In Table 3, the calls made by the SediVue Analyzer were compared to the culture results. For example, at the $10^5$ bacteria/mL concentration, 84 samples were negative by culture. Of these, 72 were called negative by the Analyzer with treatment and 12 were called positive by the Analyzer with treatment. At the $10^5$ bacterial concentration, 78 samples were positive by culture. Of these, 9 were called negative by the instrument with treatment and 69 were called positive by the instrument with treatment. The performance of SediVue Analyzer calls as compared to bacterial culture, before and after treatment, was as follows: At the $10^6$ threshold, accuracy improved from 77% to 80%, sensitivity increased from 74% to 96%, and specificity decreased from 79% to 73%. At the $10^5$ threshold, accuracy increased from 77% to 87%, sensitivity increased from 67% to 88%, and specificity decreased from 88% to 86%. At the $10^4$ threshold, accuracy increased from 71% to 77%, sensitivity increased from 58% to 73% and specificity decreased from 89% to 83%. These results indicate that the treatment of the method of the disclosure improved the performance of microscopic bacterial counting across a wide range of urinary bacterial titers. It is important to note that the blood agar method will only count viable bacteria (i.e., colony forming units), while the optical counting method on the instrument will also count nonviable bacteria.

Example 10

The performance of bacterial recognition by SediVue Analyzer, before and after treatment according to the method of the disclosure, was compared to quantitative culture. 317 fresh canine urine samples were used. For quantitative culture, the urine samples were diluted and plated onto blood agar plates as described above. Urines with a titer at or above $10^5$ bacteria/mL were deemed positive by culture, and below $10^5$ bacteria/mL were deemed negative by culture.

For automated microscopy, 165 µL of canine urine was treated with 30 µL of clearance solution (5% w/v SMOT in 500 mM citric acid) and mixed gently. The final concentration of SMOT in the treated urine sample was 0.8% w/v and citric acid was 77 mM. Then, to 165 µL of this mixture 50 µL of chelator solution (250 mM EGTA, 250 mM EDTA, 330 mM NaOH) was added and mixed gently. The final concentration of EGTA and EDTA after the addition was 58 mM each and NaOH was 77 mM. 165 µL of the resulting mixture was then placed into a SediVue® cartridge and analyzed using SediVue Analyzer. The negative control was the untreated canine urine. The instrument used an algorithm that categorized bacterial count results into three bins: negative, suspected positive (i.e., ambiguous), and positive. Results are provided in Table 4.

TABLE 4

|  |  | culture (bacteria/mL) | | | | | |
|---|---|---|---|---|---|---|---|
|  |  | Untreated | | | Treated | | |
|  |  | − | + | % | − | + | % |
| Call | − | 167 | 19 | Am = 10.1 | 181 | 11 | Am = 5.7 |
|  | ± | 22 | 10 | A = 79.8 | 7 | 11 | A = 86.4 |
|  | + | 13 | 86 | Se = 74.8 | 14 | 93 | Se = 80.9 |
|  |  |  |  | Sp = 82.7 |  |  | Sp = 89.6 |

"Am" is ambiguity; "A" is accuracy; "Se" is sensitivity; "Sp" is specificity.

As provided in Table 4, for the untreated (neat) urines, the SediVue algorithm called 32 samples (10.1%) ambiguous (±) for the presence of bacteria. With the treated urines, the number of ambiguous calls was reduced to 18 (5.7%). Therefore, the treatment of the methods of the disclosure reduced the number of ambiguous bacterial calls made by the instrument. The performance of SediVue calls as compared to bacterial culture was as follows: accuracy increased from 79.8% to 86.4%, sensitivity increased from 74.8% to 80.9% and specificity increased from 82.7% to 89.6%. In summary, the method of the disclosure using the clearance solution and chelator solution as described above improved the performance of microscopic bacterial counting.

The 32 previously untreated urines with ambiguous bacterial calls were then subjected to additional treatments. The 32 urines were treated with clearance solution and chelator solution as described above. Eight of the 32 ambiguous samples had been flagged for overcrowding. These eight samples were separately: A) diluted (between 2-fold and 10-fold) and re-analyzed on the SediVue Analyzer and B)

diluted (between 2-fold and 10-fold) prior to treatment with the clearance solution and the chelator solution, and re-analyzed on SediVue Analyzer. The results of the analyses are shown in Table 5. The number of ambiguous results fell from 32 (10.1%) without treatment, to 4 (1.3%) after treatment. Thus, dilution, or a combination of dilution and treatment can further reduce the number of ambiguous calls, as compared to treatment alone.

TABLE 5

| | | Culture $10^5$ bacteria/mL | |
|---|---|---|---|
| | | − | + |
| call | − | 18 | 2 |
| | ± | 2 | 2 |
| | + | 2 | 6 |

The previous experiment was carried out as described above on 165 µL of canine urine containing crystalline debris or on 165 µL of canine urine containing crystalline debris and mucus. Clearance solution (30 µL) and chelator solution (50 µL) were as described above. Manual light microscopy of the resulting final mixture revealed that the treatment cleared crystalline debris from the urine sample containing crystalline debris. From the urine sample containing crystalline debris and mucus, manual light microscopy of the resulting final mixture revealed that the treatment cleared both the mucus and the crystalline debris.

Example 11

To three filtered canine urine samples, 0.1% v/v of blood was added to obtain blood-containing urine samples. These blood-containing urine samples (60 µL) were each treated with 15 µL of clearance solution (SMOT at 0% w/v, 0.006% w/v, 0.012% w/v or 0.024% w/v, and 350 mM citric acid), and mixed gently. The final concentration of SMOT in the treated urine sample was 0% w/v, 0.0012% w/v, 0.0024% w/v, or 0.0049% w/v. To 75 µL of the treated sample, 15 µL of chelator solution (325 mM EDTA, 325 mM EGTA, and 500 mM NaOH) was added, followed by gentle mixing. Manual light microscopy of the resulting final mixtures revealed that all three urines were cleared of all crystals, debris and RBCs. Manual light microscopy of the resulting final mixtures revealed that final SMOT concentrations of 0.0024% w/v and above were sufficient to clear the RBCs from the urine sample.

Next, to five canine urine samples heavily crowded with crystals and debris, 0.1% v/v of blood was added to obtain blood-containing urine samples. To 60 µL of each these blood-containing urine samples, 15 µL of clearance solution (350 mM citric acid and SMOT ranging from 0.005% w/v to 0.050% w/v in increments of 0.001%) was added, and mixed gently. The final concentration of SMOT in the treated urine sample ranged from 0.001% w/v to 0.010% w/v in increments of 0.001%. To 75 µL of the treated sample, 15 µL of chelator solution (325 mM EDTA, 325 mM EGTA and 500 mM NaOH) was added, followed by gentle mixing. Manual light microscopy of the resulting final mixtures revealed that, depending on the urine sample, the urine was cleared of crystals, debris and RBCs at final SMOT concentrations of: 0.002% w/v and above, 0.007% w/v and above, 0.005% w/v and above, 0.010% w/v and above, and 0.010% w/v and above. Therefore, the final concentration of SMOT required to clear a heavily crowded urine sample from crystals, debris and RBCs can range from 0.002% w/v to 0.01 0% w/v.

In a further experiment, to canine urine samples known to be heavily crowded with crystals and debris, 0.1% v/v blood was added. To each 60 µL blood-containing urine, 15 µL of a clearance solution (3.5% w/v SMOT and 350 mM citric acid) was added, and mixed gently. To 75 µL of the treated sample, 15 µL of chelator solution (325 mM EDTA, 325 mM EGTA and 500 mM NaOH) was added, followed by gentle mixing. Manual light microscopy of the resulting final mixtures revealed that the sample urines were cleared of all crystals, debris and RBCs.

In a final experiment, to canine urine samples heavily crowded with crystals and debris, 0.1% v/v blood was added. To each 60 µL blood-containing urine, 15 µL of a clearance solution (0.05% w/v SMOT and 500 mM citrate buffer with pH 3.3) was added, and mixed gently. To 75 µL of the treated sample, 15 µL of chelator solution (1 M EDTA and 1 M NaOH) was added, followed by gentle mixing. Manual light microscopy of the resulting final mixtures revealed that the sample urines were cleared of all crystals, debris and RBCs.

Example 12

165 µL of feline urine crowded with crystals, RBCs and white blood cells was combined with 30 µL of clearance solution (5% w/v SMOT in 500 mM citric acid) and gently mixed. Then, to 165 µL of this treated sample, 50 µL of chelator solution (250 mM EGTA, 250 mM EDTA, 330 mM NaOH) was added and mixed gently. The resulting final mixture was observed by light microscopy.

Figure 11:
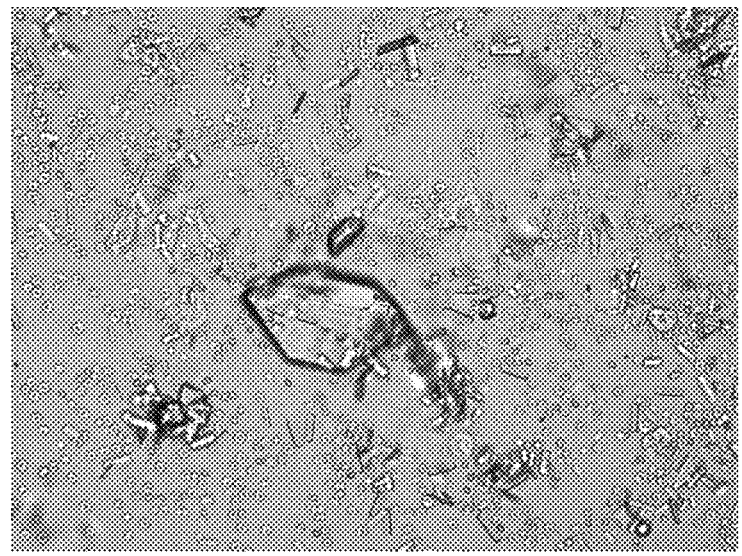
FIG. 11 illustrates treatment of feline urine crowded with crystals, red blood cells (RBCs), and white blood cells by one embodiment of the methods of the disclosure.
Figure 11:
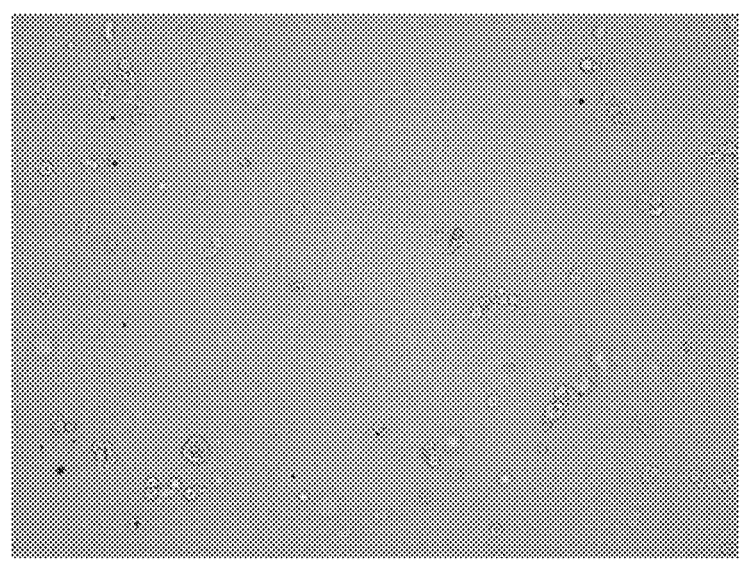

As shown in FIG. 11, urinary crystals, RBCs and white blood cells were visible in the untreated feline urine. In the feline urine treated with the method of the disclosure only the bacteria was visible, and the crystals, RBCs, and white blood cells were not visible. The treatment according to the methods of the disclosure cleared the urine of the crystals, RBCs, and white blood cells as determined by light microscopy.

The disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

All publications, patents, and patent applications cited herein are hereby incorporated herein by reference for all purposes.

What is claimed is:

1. A method of measuring an amount of bacteria in a biological sample, the method comprising:
    clearing non-bacterial particulate matter from a biological sample by contacting the biological sample with an aqueous clearance solution comprising a monounsaturated or polyunsaturated $C_{10}$-$C_{22}$ hydrocarbyl surfactant;
    generating an image of the contacted sample by a camera;
    measuring a number of pixels that correlates to the bacteria in the image; and
    correlating the number of pixels with a predetermined number of pixels to obtain the amount of bacteria in the sample; and determining the amount of bacteria in the sample.

2. The method of claim 1, wherein the surfactant is an anionic surfactant.

3. The method of claim 1, wherein the surfactant is a fatty acid amide derivative of N-methyltaurine, or a salt thereof.

4. The method of claim 3, wherein the fatty acid is a monounsaturated $C_{10}$-$C_{22}$ fatty acid.

5. The method of claim 1, wherein the surfactant is sodium methyl oleoyl taurate.

6. The method of claim 1, wherein the surfactant is a bile acid or salt thereof.

7. The method of claim 6, wherein the surfactant is selected from the group consisting of cholalic acid, sodium cholate, deoxycholic acid, and sodium deoxycholate.

8. The method of claim 1, wherein the amount of the one or more surfactants in the clearance solution is in the range of 0.0001% w/v to 50% w/v, e.g., in the range of 0.001% w/v to 50% w/v, 0.01% w/v to 50% w/v, 0.001% w/v to 10% w/v, 0.01% w/v to 7% w/v, or 0.01% w/v to 5% w/v, 0.01% w/v to 2% w/v, 0.01% w/v to 1% w/v, or 0.01% w/v to 0.1% w/v, based on the total volume of the clearance solution.

9. The method of claim 1, wherein the amount of the one or more surfactants in the clearance solution is in the range of 0.5% w/v to 50% w/v, e.g., in the range of 0.5% w/v to 10% w/v, 0.5% w/v to 7% w/v, 0.5% w/v to 5% w/v, 0.5% w/v to 2% w/v, or 0.5% w/v to 1% w/v, based on the total volume of the clearance solution.

10. The method of claim 1, wherein the amount of the one or more surfactants in the clearance solution is in the range of 1% w/v to 50% w/v, e.g., in the range of 1% w/v to 10% w/v, 1% w/v to 7% w/v, 1% w/v to 5% w/v, 1% w/v to 2% w/v, 2% w/v to 10% w/v, 2% w/v to 7% w/v, 2% w/v to 5% w/v, or 2% w/v to 3% w/v, based on the total volume of the clearance solution.

11. The method of claim 1, wherein the clearance solution is acidic.

12. The method of claim 1, wherein the clearance solution comprises a carboxylic acid or a salt thereof.

13. The method of claim 1, wherein the clearance solution comprises citric acid or a salt thereof.

14. The method of claim 12, wherein the concentration of the acid in the clearance solution is in the range of about 300 mM to 1M.

15. The method of claim 1, further comprising contacting the sample with an aqueous chelator solution.

16. The method of claim 15, wherein contacting with the chelator solution is after contacting with the clearance solution.

17. The method of claim 15, wherein contacting with the chelator solution is before contacting with the clearance solution.

18. The method of claim 15, wherein the chelator solution comprises ethylene glycol-bis(beta-aminoethyl ether)-N,N,N',N'-tetraacetic acid tetrasodium salt, ethylenediaminetetraacetic acid tetrasodium salt dehydrate, or a combination thereof.

19. The method of claim 15, wherein the chelator solution is basic.

20. The method of claim 15, wherein the chelator solution comprises sodium hydroxide solution.

21. The method of claim 1, further comprising, prior to determining the amount of bacteria in the sample, incubating the sample for 30 seconds to 30 minutes.

22. The method of claim 1, further comprising contacting the bacteria with a stain or a dye.

23. The method of claim 1, wherein the sample is not contacted with a stain or a dye prior to determining the amount of bacteria in the sample.

24. The method of claim 1, wherein determining comprises counting the bacteria and/or analyzing bacteria.

25. The method of claim 24, wherein determining is using bright-field microscopy, dark-field microscopy, or fluorescence microscopy.

26. The method of claim 1, further comprising displaying the image of the sample on a user interface.

27. The method of claim 1, wherein the predetermined number of pixels is determined by independently performing an empirical experiment using a standard sample having a known amount of bacteria.

28. The method of claim 1, the method further comprising determining bacteria shape.

29. The method of claim 1, wherein at least 10% of bacteria are viable after contacting the sample with the aqueous clearance solution, the aqueous chelator solution, or both.

30. The method of claim 29, wherein at least 50% of bacteria are viable.

31. The method of claim 1, wherein the sample is a urine sample.

32. The method of claim 31, wherein the urine sample comprises one or more contaminants selected from the group consisting of sediment, debris, mucus threads, crystals, amorphous salts, cell fragments, red blood cells, and patient cells.

33. The method of claim 1, further comprising the steps prior to contacting the biological sample with the aqueous clearance solution:
   withdrawing a portion of the biological sample;
   analyzing the portion for bacteria; and
   determining that the presence or amount of non-bacterial particulate matter interferes with the analysis for bacteria.

34. The method of claim 1, wherein the non-bacterial particulate matter is selected from the group consisting of sediment, debris, mucus threads, crystals, amorphous salts, cell fragments, red blood cells, and patient cells.

35. The method of claim 1, further comprising making a health determination based on at least the amount of bacteria in the sample.

36. A method of measuring an amount of bacteria in a biological sample, the method comprising:
   analyzing a first portion of the biological sample for bacteria in the first portion;
   determining that the presence or amount of non-bacterial particulate matter interferes with the analysis for bacteria;
   contacting a second portion of the biological sample with an aqueous clearance solution comprising one or more surfactants; and
   determining bacteria in the second portion of the biological sample by
      contacting the biological sample with an aqueous clearance solution comprising a monounsaturated or polyunsaturated $C_{10}$-$C_{22}$ hydrocarbyl surfactant;
      generating an image of the contacted sample by a camera;
      measuring a number of pixels that correlates to the bacteria in the image; and
      correlating the number of pixels with a predetermined number of pixels to obtain the amount of bacteria in the sample.

37. The method of claim 36 wherein the monounsaturated or polyunsaturated $C_{10}$-$C_{22}$ hydrocarbyl surfactant is sodium methyl oleoyl taurate.

\* \* \* \* \*